US007507417B2

(12) United States Patent  
Montagnier et al.

(10) Patent No.: US 7,507,417 B2
(45) Date of Patent: *Mar. 24, 2009

(54) IMMUNOGENIC COMPOSITIONS COMPRISING HUMAN IMMUNODEFICIENCY VIRUS TYPE 2 (HIV-2) GLYCOSYLATED AND UNGLYCOSYLATED ENVELOPE PROTEINS AND THEIR METHODS OF PREPARATION

(75) Inventors: Luc Montagnier, Le Plessis Robinson (FR); Anne G. Laurent-Crawford, Paris (FR); Bernard Krust, Paris (FR); Ara G. Hovanessian, Bourg-la-Reine (FR); Marie-Anne Rey-Cuillé, Paris (FR)

(73) Assignees: Institut Pasteur, Paris (FR); Centre National de la Recherche Scientifique, Paris (FR)

( * ) Notice: Subject to any disclaimer, the term of this patent is extended or adjusted under 35 U.S.C. 154(b) by 353 days.

This patent is subject to a terminal disclaimer.

(21) Appl. No.: 11/235,527

(22) Filed: Sep. 27, 2005

(65) Prior Publication Data

US 2007/0172927 A1 Jul. 26, 2007

Related U.S. Application Data

(60) Division of application No. 09/739,289, filed on Dec. 19, 2000, now Pat. No. 6,984,721, which is a continuation of application No. 08/321,566, filed on Oct. 27, 1994, now Pat. No. 6,197,496, which is a continuation-in-part of application No. 08/002,756, filed on Jan. 13, 1993, now Pat. No. 5,470,702, which is a division of application No. 07/356,459, filed on May 25, 1989, now Pat. No. 5,208,321, which is a continuation-in-part of application No. 07/204,346, filed on Jun. 9, 1988, now abandoned.

(51) Int. Cl.
 A61K 39/21 (2006.01)
(52) U.S. Cl. ................................... 424/208.1
(58) Field of Classification Search ................ None
 See application file for complete search history.

(56) References Cited

U.S. PATENT DOCUMENTS

| 4,839,288 | A |   | 6/1989 | Montagnier et al. |
| 4,925,784 | A |   | 5/1990 | Crow et al. |
| 5,030,719 | A |   | 7/1991 | Montagnier et al. |
| 5,051,496 | A |   | 9/1991 | Alizon et al. |
| 5,066,782 | A |   | 11/1991 | Montagnier et al. |
| 5,079,342 | A |   | 1/1992 | Alizon et al. |
| 5,208,321 | A |   | 5/1993 | Hovanessian et al. |
| 5,312,902 | A | * | 5/1994 | Montagnier et al. ........ 530/395 |
| 5,597,896 | A |   | 1/1997 | Montagnier et al. |
| 5,766,844 | A |   | 6/1998 | Sarngadharan et al. |
| 5,807,992 | A |   | 9/1998 | Hovanessian et al. |
| 5,889,158 | A |   | 3/1999 | Montagnier et al. |
| 6,056,963 | A | * | 5/2000 | Montagnier et al. ....... 424/208.1 |

FOREIGN PATENT DOCUMENTS

| EP | 0 239 425 A1 | 9/1987 |
| FR | 2 593 189 A1 | 7/1987 |
| FR | 2 593 190 A1 | 7/1987 |
| FR | 2 593 922 A1 | 8/1987 |
| FR | 2 594 229 A1 | 8/1987 |
| WO | WO 87/04459 | 7/1987 |

OTHER PUBLICATIONS

Walker, J., The Protein Protocols Handbook, Walker J., ed., Humana Press, Totowa, NJ pp. 57 and 61, 1996.
Sambrook et al., Molecular Cloning: A Laboratory Manual, Sambrook et al., eds., Cold Spring Harbor Laboratory Press, pp. 18.47-18.48, 2001.
Rey et al., 1990 J. Virol 64:922-926.
Traincard et al, 1994, AIDS Res. Human Retrov. 10(12):1659-1667.
Kodama et al., 1988, J. Virol. 62(12):4782-4785.
Clavel et al., 1987, New Engl. J. Med. 316:1180-1185.
Rey et al., 1989, J. Virol. 140:271-274.

(Continued)

*Primary Examiner*—Jeffrey S. Parkin
(74) *Attorney, Agent, or Firm*—Finnegan, Henderson, Farabow, Garrett, & Dunner, L.L.P.

(57) ABSTRACT

Four glycoproteins of apparent molecular weights 300,000, 140,000, 125,000, and 36,000 (gp300, gp140, gp125, and gp36) are detectable in human immunodeficiency virus type 2 (HIV-2) infected cells. The gp125 and gp36 are the external and transmembrane components, respectively, of the envelope glycoproteins of HIV-2 mature virions. The gp300, which is a dimeric form of gp140, the precursor of HIV-2 envelope glycoprotein, is probably formed by a pH dependent fusion in the endoplasmic reticulum. Such a doublet is also observed in cells infected with simian immunodeficiency virus (SIV), a virus closely related to HIV-2. On the other hand, the envelope glycoprotein precursor of HIV-1 does not form a dimer during its processing. Experiments carried out with various inhibitors of oligosaccharide trimming enzymes suggest that transient dimerization of the glycoprotein precursor is required for its efficient transport to the Golgi apparatus and for its processing. The gp300 is useful for detecting antibodies to HIV-2 antigens in human body fluids and for raising antibodies to gp300.

3 Claims, 6 Drawing Sheets

OTHER PUBLICATIONS

Walsh, E.E., et al., 1985, "Purification and characterization of the respiratory syncytial virus fusion protein," J. Gen. Virol. 66:409-415.
Chakrabarti et al., 1987, "Sequence of simian immunodeficiency virus from macaque and its relationship to other human and simian retroviruses," Nature 328:543-547.
Harlow et al., eds. 1988, Antibodies: A Laboratory Manual, Cold Spring Harbor Laboratory, pp. 100-123.
Norley and Kurth, 1992, "Vaccination against HIV," Immunobiol. 184:193-207.
Gnann et al., 1987, "Synthetic peptide immunoassay distinguishes HIV type 1 and HIV type 2 infections," Science 237:1346-1349.
Veronese et al. J. Virology, vol. 63(3):1416-1419 (1989).
Galfré et al., 1981, Meth. Enzymol. 73:3-46.
Strongin, W., 1993, Laboratory Diagnosis of Viral Infections, Lennette, E., ed. Marcek Dekker, Inc., New York, pp. 211-219.
Clavel et al., 1986, Science 233:343-346.
Clavel et al., 1986, Nature 324:691-695.
Laurence, J., 1988, AIDS Res. Human Retro. 4:vii-viii.
Goodenow et al., 1989, J. Acquir, Immune Defic. Syndr. 2:344-352.
Holland et al., 1992, Curr. Topics Microbiol. Immunol. 176:1-19.
Goa et al., 1994, J. Virol. 68:7433-7444.
Rey et al., 1989, Virol. 173:258-267.
Chakrabarti et al., 1900, Virol. 178:134-142.
Parekh et al., 1991, AIDS 5:1009-1013.
Doms et al., 1991, Mechanisms and specificity of HIV entry into host cells, N. Duzgunes, ed. Plenum Press, NY, pp. 302-219.
Tedder et al., 1988, The Lancet (Oct. 22) 927-930.
Norrby et al., 1991, AIDS Res. Human Retro. 7:279-285.
Kanki, P.J., et al., 1985, "Antibodies to simian T-lymphotropic retrovirus type III in African green monkeys and recognition of STLV-III viral proteins by AIDS and related sera.", Lancet (Jun. 8) pp. 1330-1332.
Galfré, G., and C. Milstein, 1975, "Preparation of monoclonal antibodies: strategies and procedures.", Meth. Enzymol. 73:3-46.
Earl, P.L., et al., 1990, "Oligiomeric structure of the human immunodeficiency virus type 1 envelope glycoprotein.", Proc. Ntl. Acad. Sci. USA 87:648-652.
McGuire, T.C., et al., 1992, "Transmembrane protein oligomers of caprine arthritis-encephalitis lentivirus are immunodominant in goats with progressive arthritis.", J. Virol. 66(5):3247-3250.

* cited by examiner

IMMUNOGENIC COMPOSITIONS COMPRISING HUMAN IMMUNODEFICIENCY VIRUS TYPE 2 (HIV-2) GLYCOSYLATED AND UNGLYCOSYLATED ENVELOPE PROTEINS AND THEIR METHODS OF PREPARATION

CROSS-REFERENCE TO RELATED APPLICATIONS

This is a division of application Ser. No. 09/739,289, filed Dec. 19, 2000 now U.S. Pat. No. 6,984,721 (allowed), which is a continuation of application Ser. No. 08/321,566, filed Oct. 27, 1994 (now U.S. Pat. No. 6,197,496), which is a continuation-in-part of application Ser. No. 08/002,756, filed Jan. 13, 1993 (now U.S. Pat. No. 5,470,702), which is a divisional of application Ser. No. 07/356,459, filed May 25, 1989 (now U.S. Pat. No. 5,208,321), which is a continuation-in-part of application Ser. No. 07/204,346, filed Jun. 9, 1988 (abandoned), all of which are hereby incorporated herein by reference.

BACKGROUND OF THE INVENTION

This invention relates to viral proteins and glycoproteins, to compositions containing these proteins, to methods of preparing the proteins, and to their use in detecting viral infection.

The etiological agent of acquired immunodeficiency syndrome (AIDS) is the retrovirus referred to as human immunodeficiency virus (HIV) (Montagnier et al., 1984). To date, two related but distinct viruses, HIV-1 and HIV-2, have been identified (Barre-Sinoussi et al., 1983; Popovic et al., 1984; Levy et al., 1984; Wain-Hobson et al., 1985a; Clavel et al., 1986a; Brun-Vezinet et al., 1987; Guyader et al., 1987). HIV-2 is closely related to simian immunodeficiency virus (SIV), which causes an AIDS-like disease in macaques (Daniel et al, 1985; Sonigo et al., 1985; Chakrabarti et al., 1987).

HIV-1, HIV-2, and SIV show all the features of retrovirus family members (Wain-Hobson et al., 1985b; Montagnier and Alizon, 1987; Guyader et al., 1987; Chakrabarti et al., 1987). Their proviral genomes contain two long terminal repeats (LTRs) and three essential genes required for virus replication encoding the viral internal structural proteins (gag), the reverse transcriptase (pol), and the envelope glycoproteins (env) of the virus. In addition to these genes, both HIVs and SIV contain additional genes encoding the proteins that regulate viral expression (tat and art/trs) and three other genes encoding proteins of unknown function (Q or sor, F or 3'orf, and R). The only notable difference in the genetic organizations of HIV-1, HIV-2, and SIV resides in the open reading frame referred to as X, which is absent in HIV-1.

Alignments of the nucleotide sequences of HIV-1, HIV-2, and SIV reveal a considerable homology between HIV-2 and SIV. These two viruses share about 75% overall nucleotide sequence homology, but both of them are only distantly related to HIV-1 with about 40% overall homology (Guyader et al., 1987; Chakrabarti et al., 1987). At the protein level, the gag and pol proteins of HIV-1, HIV-2, and SIV are antigenically cross-reactive, whereas env proteins are cross-reactive only between HIV-2 and SIV (Clavel et al., 1986b, 1987).

HIV-1, HIV-2, and SIV are both tropic and cytopathic for CD4 positive T lymphocytes (Dagleish et al., 1984; Klatzman et al., 1984; McDougal et al., 1985; Clavel et al., 1986b, 1987; Kannagi et al., 1985; Fultz et al., 1986). A great number of studies have indicated that CD4 functions as the cellular receptor for HIV-1 (for references see Weiss, 1988).

The HIV-1 env gene codes for a 160 Kd glycoprotein that is proteolytically cleaved to yield the extracellular and transmembrane proteins, gp120 and gp41, respectively (Montagnier et al., 1985). It has been demonstrated that HIV-1 recognition of CD4 is mediated by gp120. This complex gp120-CD4 can be identified by co-immunoprecipitation using antibodies specific for the CD4 antigen (McDougal et al., 1986). Following the binding of gp120 to CD4, the entry of HIV-1 into the cell might occur by viral envelope cell membrane fusion (Lifson et al., 1986; Sodroski et al., 1986; Stein et al., 1987; McClure et al., 1988). A putative fusogenic domain in gp41 (Kowalski et al., 1987), which has a sequence homologous to other fusion peptides (Phe-Leu-Gly; Gallaher, 1987), might provide at least one HIV fusion site necessary for this process (Marsh and Dalgleish, 1988).

In the case of HIV-2, a high molecular weight protein of about 130 Kd to about 140 Kd has been associated with the major envelope glycoprotein (Clavel et al., *Science*, 233: 343-346, 1986). Another glycoprotein having a molecular weight of 120 Kd has been associated with the external glycoprotein of HIV-2 (Guyader et al., *Nature*, 362: 662-669, 1987). Nevertheless, detailed information for HIV-2 envelope proteins and glycoproteins and their cleavage products and precursors is lacking.

There exists a need in the art for additional information on the structure and in vivo processing of HIV-2 proteins, and especially HIV-2 envelope proteins and glycoproteins. Such information would aid in identifying HIV-2 infection in individuals. In addition, such findings could aid in elucidating the mechanism by which HIV-2 infection and virus proliferation occur and thereby make it possible to devise modes of intervening in viral processes.

SUMMARY OF THE INVENTION

This invention aids in fulfilling these needs in the art by providing HIV-2 envelope proteins and glycoproteins in purified form. Four glycoproteins of apparent molecular weights 300,000, 140,000, 125,000, and 36,000 daltons (gp300, gp140, gp125, and gp36) are detectable in human immunodeficiency virus type 2 (HIV-2) infected cells. The gp125 and gp36 are the external and transmembrane components, respectively, of the envelope glycoproteins of HIV-2 mature virions. It has now been discovered that the gp300 is a dimeric form of gp140, which is the precursor of HIV-2 envelope glycoprotein. This invention thus provides gp300 glycoprotein of HIV-2 and human retroviral variants of HIV-2 in purified form.

This invention also provides proteins of HIV-2 or of a human retroviral variant of HIV-2 having apparent molecular weights of about 200 Kd (p200) and about 90 to about 80 Kd (p90/80). These proteins are substantially unglycosylated and are in a purified form.

A similar high molecular weight glycoprotein of Simian Immunodeficiency Virus (SIV) or of a Simian retroviral variant of SIV has also been discovered. This glycoprotein is a precursor of an envelope glycoprotein of SIV and has an apparent molecular weight of about 300 Kd ($gp300_{SIV}$). This glycoprotein is also provided in a purified form.

This invention also provides labeled gp300 of HIV-2 and gp300 of SIV. Preferably, the labeled glycoproteins are in purified form. It is also preferred that the labeled glycoprotein is capable of being immunologically recognized by human body fluid containing antibodies to HIV-2 or SIV. The gp300 glycoproteins can be labeled, for example, with an immunoassay label selected from the group consisting of radioactive, enzymatic, fluorescent, chemiluminescent labels, and chromophores.

Immunological complexes between the proteins and glycoproteins of the invention and antibodies recognizing the proteins and glycoproteins are also provided. The immunological complexes can be labeled with an immunoassay label selected from the group consisting of radioactive, enzymatic, fluorescent, chemiluminescent labels, and chromophores.

Furthermore, this invention provides a method for detecting infection of cells by human immunodeficiency virus type-2 (HIV-2). The method comprises providing a composition comprising cells suspected of being infected with HIV-2, disrupting cells in the composition to expose intracellular proteins, and assaying the exposed intracellular proteins for the presence of gp300 glycoprotein of HIV-2. The exposed intracellular proteins are typically assayed by electrophoresis or by immunoassay with antibodies that are immunologically reactive with gp300 glycoprotein of HIV-2.

This invention provides still another method of detecting antigens of HIV-2, which comprises providing a composition suspected of containing antigens of HIV-2, and assaying the composition for the presence of gp300 glycoprotein of HIV-2. The composition is typically free of cellular debris.

A method of distinguishing HIV-2 infection from HIV-1 infection in cells suspected of being infected therewith has also been discovered. The method comprises providing an extract containing intracellular proteins of the cells, and assaying the extract for the presence of gp300 glycoprotein. The gp300 is characteristic of HIV-2, but the glycoprotein has not been found in extracts of HIV-1 cell cultures.

In addition, this invention provides a method of making gp300 glycoprotein of HIV-2, which comprises providing a composition containing cells in which HIV-2 is capable of replicating, infecting the cells with HIV-2, and culturing the cells under conditions to cause HIV-2 to proliferate. The cells are then disrupted to expose intracellular proteins. The gp300 glycoprotein is recovered from the resulting exposed intracellular proteins.

This invention also provides an in vitro diagnostic method for the detection of the presence or absence of antibodies which bind to an antigen comprising the proteins or glycoproteins of the invention or mixtures of the proteins and glycoproteins. The method comprises contacting the antigen with a biological fluid for a time and under conditions sufficient for the antigen and antibodies in the biological fluid to form an antigen-antibody complex, and then detecting the formation of the complex. The detecting step can further comprise measuring the formation of the antigen-antibody complex. The formation of the antigen-antibody complex is preferably measured by immunoassay based on Western Blot technique, ELISA (enzyme linked immunosorbent assay), indirect immunofluorescent assay, or immunoprecipitation assay.

A diagnostic kit for the detection of the presence or absence of antibodies, which bind to the proteins or glycoproteins of the invention or mixtures of the proteins and glycoproteins, contains antigen comprising the proteins, glycoproteins, or mixtures thereof and means for detecting the formation of immune complex between the antigen and antibodies. The antigens and the means are present in an amount sufficient to perform the detection.

Precursors of the envelope glycoproteins of HIV-2 and SIV can be prepared according to this invention. Specifically, this invention provides a method of preparing the precursors, which comprises providing an extracellular composition containing gp300 glycoprotein of HIV-2 or SIV at a pH of at least about 6.5. The pH of the composition is then lowered to a value of about 4 to about 6.0 in order dissociate the gp300 glycoprotein into gp140 glycoprotein of HIV-2 or gp140 glycoprotein of SIV.

Finally, this invention provides an immunogenic composition comprising a protein or glycoprotein of the invention in an amount sufficient to induce an immunogenic response in vivo, in association with a pharmaceutically acceptable carrier therefor.

The proteins and glycoproteins of this invention are thus useful as a portion of a diagnostic composition for detecting the presence of antibodies to antigenic proteins associated with HIV-2 and SIV. In addition, the proteins and glycoproteins can be used to raise antibodies for detecting the presence of antigenic proteins associated with HIV-2 and SIV. The proteins and glycoproteins of the invention can be also employed to raise neutralizing antibodies that either inactivate the virus, reduce the viability of the virus in vivo, or inhibit or prevent viral replication. The ability to elicit virus-neutralizing antibodies is especially important when the proteins and glycoproteins of the invention are used in vaccinating compositions.

BRIEF DESCRIPTION OF THE DRAWINGS

This invention will be described in greater detail by referring to the drawings in which:

FIG. 3($a$) is a fluorograph of dissociated gp300 of HIV-2;

FIG. 3($b$) and FIG. 3($c$) are fluorographs of denatured gp300 of HIV-2;

DETAILED DESCRIPTION OF PREFERRED EMBODIMENTS

As a result of this invention, the processing of HIV-2 envelope glycoproteins has now been characterized. Four glycoproteins referred to as gp300, gp140, gp125, and gp36 are synthesized in HIV-2 infected cells. The gp125 and gp36 correspond to the external and transmembrane glycoproteins of HIV-2 virion, whereas gp300 and gp140 are only detectable in infected cells. The gp300 is a dimeric form of gp140, which is the immature precursor of HIV-2 envelope glycoprotein. This dimer is very stable since it resists ionic and non-ionic detergents, high salt, 4M urea, and reducing agents. However, the dimer can be dissociated in acidic pH to yield gp140.

Dimerization occurs in the endoplasmic reticulum after the removal of glucose residues by glucosidases I and II, and after the action of Golgi mannosidases, the dimer becomes dissociated probably due to a shift in pH of the environment in trans Golgi. Finally, proteolytic cleavage of the mature precursor occurs outside the Golgi.

Transient dimer formation of the glycoprotein precursor seems to be an intrinsic property of the polypeptide moiety of HIV-2 envelope. This is a novelty in the mechanism of glycoprotein processing with N-linked oligosaccharide chains. It is hypothesized that conformational modifications brought about by the formation of this dimer are necessary for transport of the glycoprotein precursor to the Golgi apparatus.

I. Identification of the HIV-2 Envelope Glycoproteins

Recently, it has been reported that the envelope gene of HIV-2 (ROD isolate) encodes a precursor glycoprotein that is then cleaved proteolytically to yield a 120 Kd extracellular glycoprotein and a 36 Kd transmembrane glycoprotein (Clavel et al., 1986a and 1986b). To identify the precursors of the HIV-2 glycoproteins, viral proteins in infected cells as well as in virus particles were studied. For comparison, the synthesis of HIV-1 proteins in cells infected with HIV-1 (BRU isolate) were also studied. The results are shown in FIG. 1 and were obtained as follows.

Figure 1A:
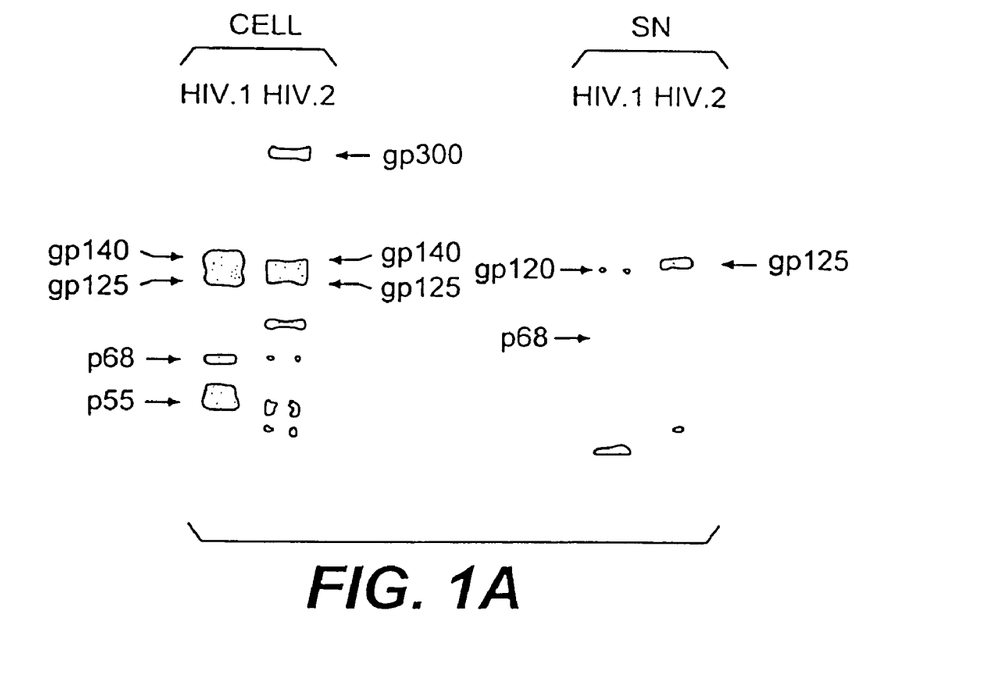
FIG. 1A is a fluorograph in which high molecular weight proteins of HIV-1 and HIV-2 are compared after electrophoresis in a polyacrylamide SDS gel.

A. Comparison of High Molecular Weight Proteins of HIV-1 and HIV-2 (FIG. 1A)

CEM cells infected with HIV-1 or HIV-2 were labeled with $^{35}$S-methionine (200 µCi/ml; 4×10$^6$ cells/ml) for 18 hours. Extracts from these infected cells (CELL) and their corresponding culture medium (SN) were purified on specific immunoaffinity columns:

HIV-1 serum-Sepharose specific for HIV-1 proteins (Krust et al., 1988), and

HIV-2 serum-Sepharose specific for HIV-2 proteins.

(See "Experimental Procedures").

These purified proteins were analyzed by electrophoresis in a 7.5% polyacrylamide SDS-gel containing 6M urea. A fluorograph of the gel is presented in FIG. 1. The sizes of the HIV-1 and HIV-2 proteins are indicated on the left and right of the lanes shown in FIG. 1.

Referring to FIG. 1A, the p68 and p55 are the reverse transcriptase and the gag precursor, respectively. The gp160 and gp120 are the glycoprotein precursor of HIV-1 envelope and its cleaved product.

Three major high molecular weight glycoproteins of 300, 140, and 125 Kd are detectable in HIV-2 infected cells (FIG. 1A). The proteins are specific to HIV-2 because they are absent in non-infected cells and because they could be consistently identified by all HIV-2, but not HIV-1, seropositive sera in an immunoprecipitation assay (data not shown).

In side by side comparison, the electrophoretic mobility of these three HIV-2 proteins is clearly different from that of the 160 Kd HIV-1 precursor glycoprotein (gp160) and one of its cleaved products, 120 Kd external envelope glycoprotein (gp120; FIG. 1A). It should be noted that the resolution of the 140 and 125 Kd proteins of HIV-2 from one another can be clearly observed in polyacrylamide-SDS gels containing a high concentration of urea. In the absence of urea, these proteins migrate as a thick band. The 300 and 140 Kd proteins are only detectable in infected cells, whereas the 125 Kd protein is detectable both in infected cells as well as in the virus (FIG. 1A).

B. Identification of HIV-2 Glycoproteins (FIG. 1B)

Figure 1B:
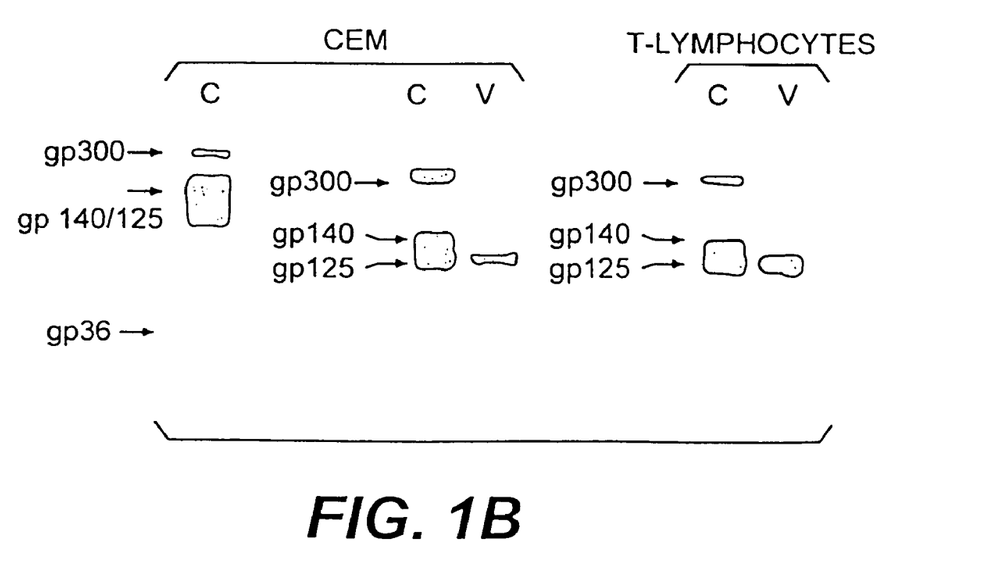
FIG. 1B depicts the result of electrophoresis of HIV-2 glycoproteins in an acrylamide gel.

The glycosylation of the 300, 140, and 125 Kd proteins was demonstrated by metabolic labeling with $^3$H-glucosamine (FIG. 1B). More particularly, HIV-2 CEM cells and T-lymphocytes were labeled with $^3$H-glucosamine (200 µCi/ml; 4×10$^6$ cells/ml) for 18 hours. Extracts from infected cells (lanes C) and culture medium containing virus (lanes V) were purified on the HIV-2 serum-Sepharose column. The labeled proteins were analyzed by electrophoresis in a 7.5% gel. The lane on the far left depicts the result of electrophoresis in a 12.5% acrylamide gel and shows the presence of gp36. The gp36 is only slightly glycosylated and its detection required longer exposure times. Specifically, this part of the Figure had to be overexposed to see gp36; for this reason gp140/gp125 are resolved as a thick band.

The presence of gp300 and gp140 is not restricted to infected CEM cells. They are also detectable in HIV-2 infected T4 lymphocytes as depicted in FIG. 1B. As in CEM cell cultures, gp300 and gp140 are detectable only in infected cells, whereas gp125 is present both in cells and in HIV-2 particles.

These results indicate that among the glycoproteins detectable in HIV-2 infected cells, gp125 and gp36 correspond to the virion envelope, whereas gp300 and gp140 might be precursors of the envelope glycoproteins.

C. Characterization of gp300 and gp140 (FIG. 2)

The proteins gp300, gp140, and gp125 were labeled with $^{35}$S-methionine and analyzed by two dimensional gel electrophoresis. The patterns of resolution that were obtained indicated that gp300 and gp140 are closely related.

More particularly, $^{35}$S-methionine labeled gp300, gp140, and gp125 purified from HIV-2 infected CEM cells (CELL) and culture medium containing virus (SN) prepared in the same manner as the experiments reported in FIG. 1 were analyzed by two dimensional gel electrophoresis (See "Experimental Procedures"). The pH gradient obtained by isoelectric focusing (first dimension) is shown in FIG. 2. In the second dimension, proteins were resolved on a 7.5% polyacrylamide-SDS gel containing 6M urea. Fluorographs of the gels are presented in FIG. 2.

Figure 2:
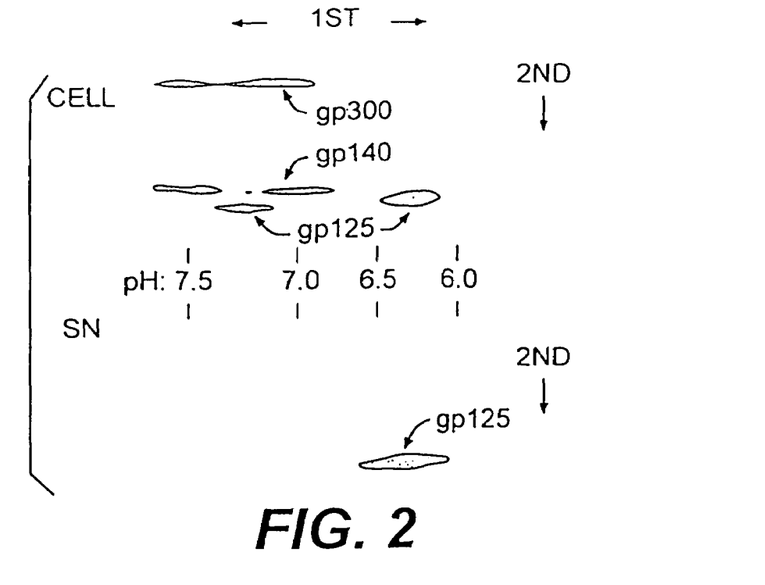
FIG. 2 depicts the result of two dimensional gel electrophoretic analysis of HIV-2 glycoproteins.

Both proteins were resolved as an heterogeneous subspecies with identical isoelectric points (pI) in the pH range of 6.8 to 7.8 (FIG. 2). This similarity between gp140 and gp300 suggested that gp300 is a dimeric form of gp140 (see below).

The gp125, which is present in both infected cells and in virus particles, exhibited less heterogeneity and migrated with pI values between 6.2 to 6.5. In infected cells, there was a minor subspecies of gp125 with a pI value of 7.2 to 7.3. This basic gp125 is not incorporated into the HIV-2 virion. Thus it might represent a glycoprotein that is not processed properly. The acidic nature of the mature gp125 might be due to the addition of sialic acid on some of its carbohydrate side chains during the processing of the envelope glycoprotein.

D. Dissociation of the Native (a) and the Denatured (b and c) gp300 (FIG. 3)

The gp300 is very stable since it resists ionic (1% SDS) and non-ionic (2% Triton X-100) detergents, urea %,(2-6M), high salt (1M NaCl), and reducing agents (1% β-mercaptoethanol). However, it was possible to demonstrate that gp300 could be dissociated into gp140 in acidic pH. In these experiments, immunoaffinity column bound proteins were incubated in acetate buffer at pH values varying between 4 to 7.

These samples were then analyzed by polyacrylamide gel electrophoresis. Fluorographs of the gels are shown in (a), (b), and (c) in FIG. 3. In section (c), the band of gp300 and the dissociated gp140 were quantified by densitometric scanning of the fluorograph. More particularly, the gels were prepared as follows.

(a) $^{35}$S-methionine labeled extracts from HIV-2 infected CEM cells were purified on the HIV-2 serum-Sepharose column. This sample was then divided into two equal aliquots: one was incubated in the binding buffer, FIG. 3(a), lane 1, whereas the other one was incubated in buffer containing 30 mM sodium acetate pH 4.0, 0.2 mM PMSF, 100 units/ml aprotinin and 5 mM β-mercaptoethanol, FIG. 3(a), lane 2. After 1 hour at 37° C., the acidic medium was neutralized and both samples were analyzed by electrophoresis.

Figure 3A:
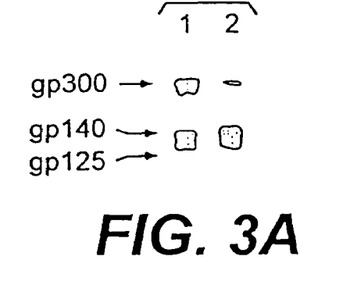
Figure 3B:
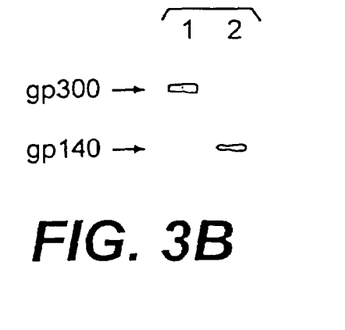

(b) Purified and lyophilized $^{35}$S-methionine labeled gp300 was suspended in 100 μl of the sodium acetate buffer pH 4.0 as above FIG. 3(b), lane 2. Incubations were carried out for 30 minutes at 37° C. before addition of 2-fold electrophoresis sample buffer containing 2M urea. In lane 1 of FIG. 3(b), the lyophilized gp300 was directly suspended in the electrophoresis sample buffer.

Figure 3C:
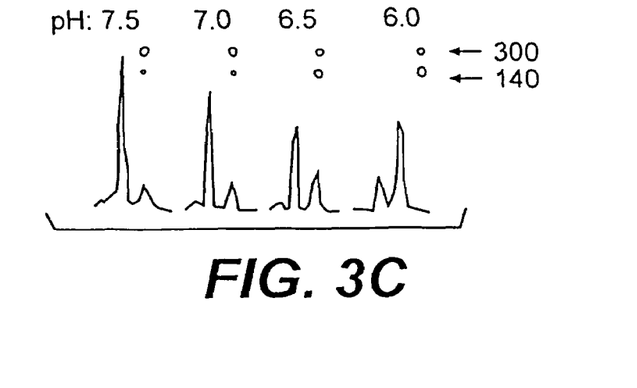

(c) The purified and lyophilized $^{35}$S-methionine labeled gp300 was suspended in solution containing 30 mM Tris-HCl, 0.2 mM PMSF and 100 units/ml aprotinin and buffered with HCl at pH 7.5, 7.0, 6.5 and 6.0 (as indicated). After 60 minutes at 37° C., two fold electrophoresis sample buffer was added and the samples were analyzed by electrophoresis.

FIG. 3(a) shows that the band of gp300 shifted to the position of gp140 when the sample was incubated at pH 4. Further experiments were carried out using purified preparations of gp300 obtained by preparative gel electrophoresis. Such denatured samples of gp300 were dissociated completely in acetate buffer at pH 6.0, FIG. 3(b). The efficiency of dissociation of the purified gp300 was probably due to a decrease in the pH along with the presence of residual SDS in the lyophilized sample, since column-bound native gp300 did not dissociate in the same buffer at pH values higher than pH 5 (data not shown).

In Tris-HCl buffer, the dissociation was less efficient. At pH 7.5 there was only a slight dissociation of gp300 to gp140, but it increased with decreasing pH values. In Tris buffer at pH 6.0, the dissociation was about 80%, (FIG. 3(c)). During dissociation of the pure gp300 in either acetate or Tris-HCl buffer no proteins other than gp140 were detectable (experiments carried out in 15% polyacrylamide gels; data not shown).

These results indicate that gp300 is a dimeric form of gp140, the precursor of HIV-2 envelope glycoprotein. Thus, it seems most likely that during the processing of the envelope glycoprotein, two molecules of gp140 become fused by a pH-dependent mechanism.

Figure 4:
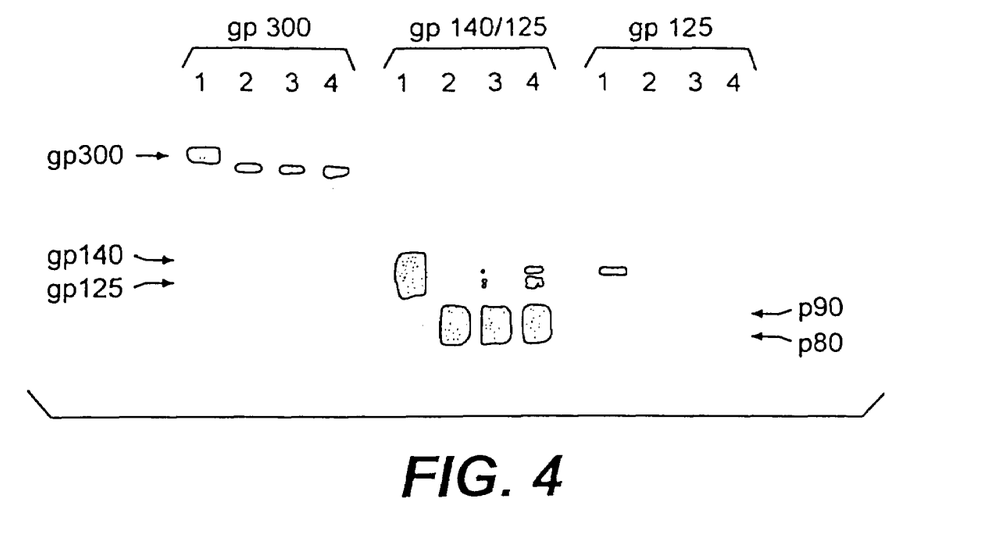
FIG. 4 shows the result of electrophoresis of HIV-2 glycoproteins after the glycoproteins were digested with beta-N-acetylglucosaminidase H (endo H)
Figure 5:
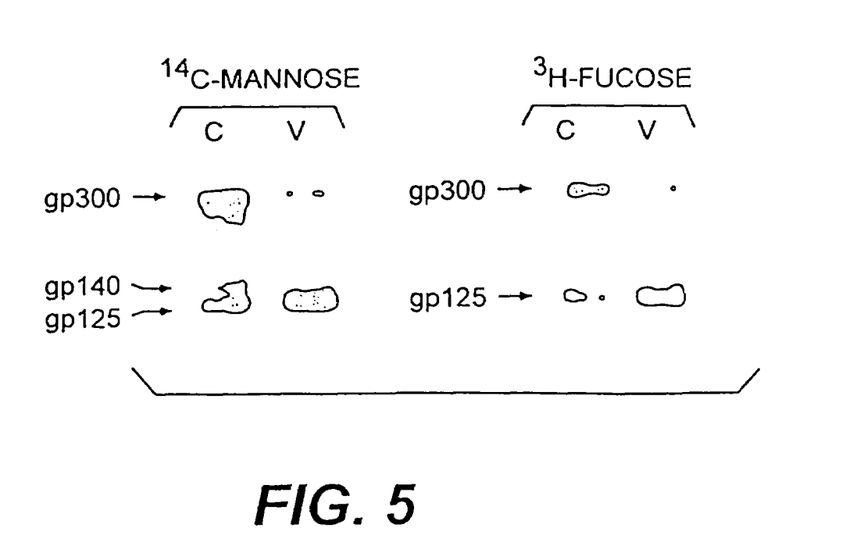
FIG. 5 is a fluorograph of a polyacrylamide gel after electrophoresis of HIV-2 glycoproteins, which were isotopically labeled with $^{14}$C-mannose or $^{3}$H fucose.

E. Characterization of the Oligosaccharide Side Chains of HIV-2 Glycoproteins (FIGS. 4 & 5)

Digestion with endo β-N-acetylglucosaminidase H (endo H) demonstrated the presence of N-linked oligosaccharides of the high mannose type on HIV-2 glycoproteins. The gp300, the gp140+gp125, and the gp125 were purified by immunoaffinity chromatography and preparative electrophoresis. (See "Experimental Procedures"). The lyophilized samples were suspended in endo H digestion buffer, which does not promote the dissociation of gp300 to gp140. The procedure was carried out as follows.

Purified and lyophilized gp300, gp140/gp125, and gp125 ("Experimental Procedures") were suspended in buffer containing 150 mM sodium citrate pH 5.5, 0.1% SDS (w/v), 0.5 mM PMSF before heating for 2 minutes at 90° C. Aliquots of these samples were then incubated (2 hours, 30° C.) without (lane 1, FIG. 4), or with 0.4 milli-units of endo-H (lane 2, FIG. 4), 2 milli-units of endo-H (lane 3, FIG. 4), and 10 milli-units of endo-H (lane 4, FIG. 4). All the reactions were stopped by the addition of two fold electrophoresis sample buffer. Electrophoresis was as previously described in relation to FIG. 1. Fluorographs of the different gels are shown in FIG. 4. The arrows p90 and p80 on the right indicate the position of the digested product. Conditions for endo-H digestion were as described (Tarentino et al., 1974).

Upon endo H digestion, the electrophoretic mobility of gp300 was reduced to a protein of 200-250 Kd. A small fraction of gp300 that had become dissociated into gp140, was digested to give rise to a 80 Kd protein (FIG. 4, section gp300, lane 4).

The gp140+gp125 sample was digested by endo H into 90 and 80 Kd proteins whereas gp125 was converted into a 90 Kd protein (FIG. 4, sections gp140/125 and gp125). These results indicate that endo H digestion of gp140 and gp125 give products of molecular weight 80 and 90 Kd, respectively. The resistance to endo H digestion of gp125 relative to gp140 is probably due to the conversion of some high mannose type oligosaccharide side chains into complex oligosaccharides during processing of the envelope glycoprotein (Kornfeld and Kornfeld, 1985).

Metabolic labeling of cells was carried out with $^{14}$C-mannose and $^3$H-fucose. More particularly, HIV-2 infected CEM cells were labeled (18 hours) with $^{14}$C-mannose 25 μCi/ml; 4×10$^6$ cells/ml) or $^3$H-fucose (200 μCi/ml; 4×106 cells/ml). Extracts from infected cells (lanes C, FIG. 5) and culture medium containing virus (lanes V, FIG. 5) were purified on HIV-2 serum-Sepharose. Labeled glycoproteins were then analyzed by polyacrylamide gel electrophoresis. A fluorograph is shown in FIG. 5.

Referring to FIG. 5, it will be apparent that metabolic labeling resulted in the incorporation of mannose into gp300, gp140, and gp125 whereas only gp300 and gp125 were able to incorporate fucose. Fucose residues are normally transferred on oligosaccharide chains late in the glycosylation cycle, after the action of trimming enzymes of the endoplasmic reticulum and Golgi apparatus (Kornfeld and Kornfeld, 1985; Fuhrmann et al., 1985). The fact that gp140 does not contain fucose residues was consistent with it being the precursor of gp300 and gp125.

Figure 6:
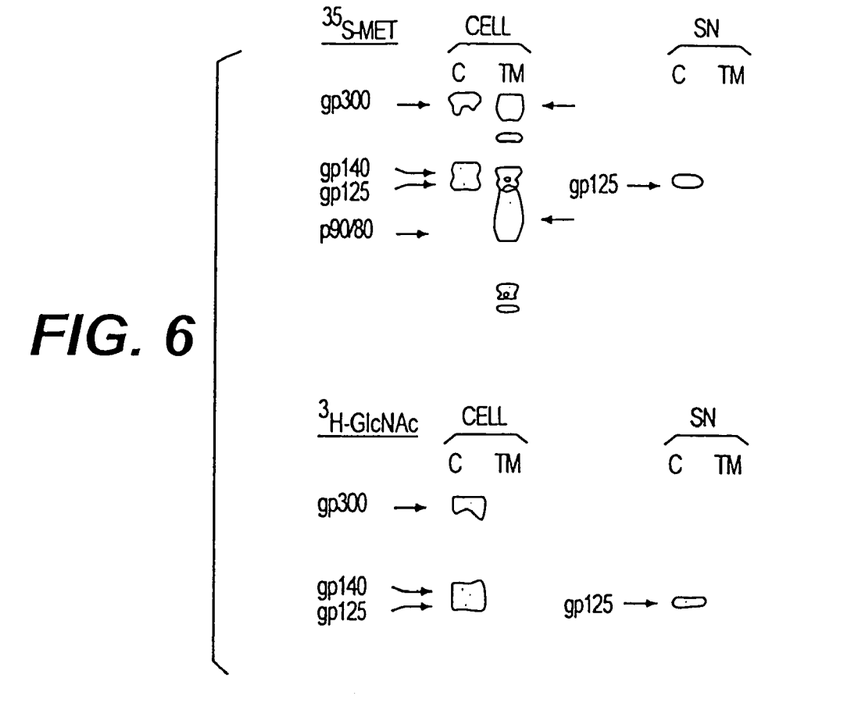
FIG. 6 shows the result of electrophoresis of HIV-2 envelope proteins obtained from cultures in which N-linked glycosylation was inhibited by the antibiotic tunicamycin.

F. The Effect of Glycosylation Inhibitor Tunicamycin on the Processing of HIV-2 Glycoproteins (FIG. 6)

All glycoproteins carrying N-linked glycans derive their oligosaccharide moiety from the lipid-linked oligosaccharide, Glc$_3$Man$_q$-GlcNAc$_2$-pp-Dolichol, through a reaction carried out by protein-oligosaccharidyl transferase, which catalyzes the en bloc transfer of oligosaccharide chains to asparagine residues (for references, see Kornfeld and Kornfeld, 1985). Tunicamycin blocks such N-linked glycosylation since it inhibits the production of N-acetylglucosamine pyrophosphoryldolichol, the first step in the assembly of lipid-linked oligosaccharides (Li et al, 1978; Heifetz et al., 1979).

In the presence of 2 μg/ml tunicamycin, the overall N-linked glycosylation of HIV-2 envelope glycoproteins was completely blocked in infected CEM cells. This was demonstrated by the lack of $^3$H-glucosamine incorporation in viral glycoproteins, gp300, gp140, and gp125. Inhibition of N-linked glycosylation by tunicamycin was carried out as follows.

HIV-2 infected cells in the absence (lanes C, FIG. 6) or presence (TM, FIG. 6) of tunicamycin (2 μg/ml) were labeled with $^{35}$S-methionine (panel "$^{35}$S-met"; 200 μCi/ml; 4×10$^6$ cells/ml) or with $^3$H-glucosamine (panel "$^3$H-GLcNAc"; 200

μCi/ml; 4×10⁶ cells/ml) for 16 hours. Cells treated with tunicamycin were first incubated (37° C.) with the antibiotic (2 μg/ml) for 2 hours before labeling with $^{35}$S-methionine or $^{3}$H-glucosamine. Extracts from infected cells (CELL) and from the culture medium containing virus (SN) were purified by HIV-2 serum-Sepharose and analyzed by polyacrylamide 7.5% gel electrophoresis. Fluorographs of the gels are presented in FIG. 6. The position of the unglycosylated envelope precursor (p90/80) and the unglycosylated dimer (200 Kd) are indicated by the small arrows on the right. These 90/80 Kd and 200 Kd proteins do not incorporate $^{3}$H-glucosamine (panel $^{3}$H-GlcNAc, cell lane TM).

Under these experimental conditions, protein synthesis was not affected in infected cells treated with tunicamycin (data not shown). Such cultures isotopically labeled with $^{35}$S-methionine accumulated two major proteins of apparent sizes 200 and 80-90 Kd, which migrated as wide bands (FIG. 6). The molecular weights of these proteins coincide well with endo H digestion products of gp300, gp140, and gp125 (FIG. 4), thus suggesting that the 200 and 80-90 Kd proteins correspond to unglycosylated forms of HIV-2 envelope glycoproteins. The molecular weight of the 80-90 Kd protein corresponds to the expected molecular weight of unglycosylated HIV-2 envelope precursor estimated from its nucleic acid sequence (Guyader et al., 1987). The 200 Kd protein is probably the dimeric form of the unglycosylated envelope precursor. These results confirm that HIV-2 envelope proteins have N-linked polysaccharide chains.

Besides inhibition of glycosylation, tunicamycin treatment inhibits the processing and export of the envelope glycoprotein since the 80-90 Kd protein was not found in the extracellular medium (FIG. 6, lanes SN). Oligosaccharide chains of HIV-2 envelope proteins, therefore, are probably involved in the cellular transport through the Golgi apparatus. The absence of unglycosylated forms of the envelope protein in the extracellular medium of tunicamycin treated cells might also be due to its rapid degradation. Several reports have suggested that the unglycosylated form of a protein is more sensitive to proteases than its glycosylated form (Olden et al., 1978; Schwartz et al., 1976). Accordingly, the small molecular weight proteins in $^{35}$S-methionine labeled cells cultured with tunicamycin might represent partially degraded products of the unglycosylated envelope protein (FIG. 6).

Figure 7:
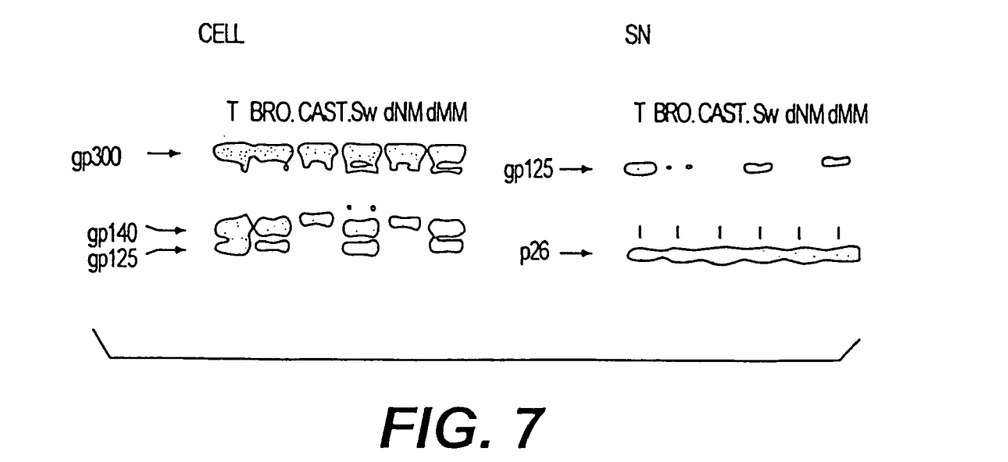
FIG. 7 is a fluorograph of a polyacrylamide gel after electrophoresis of HIV-2 envelope glycoproteins obtained from cell cultures with and without oligosaccharide trimming inhibitors.

G. Effect of Oligosaccharide Trimming Inhibitors on the Synthesis of HIV-2 Glycoproteins (FIG. 7)

Asparagine-linked oligosaccharides ($Glc_3Man_qGlcNAc_2$) of glycoproteins undergo extensive modifications or processing following their attachment to nascent proteins (reviewed by Kornfeld and Kornfeld, 1985). The trimming reactions occur in the lumen of the rough endoplasmic reticulum (RER) and in the Golgi apparatus by specific glucosidases and mannosidases.

Processing of oligosaccharide chains of glycoproteins can be manipulated with the aid of specific inhibitors of the trimming glucosidases and mannosidases (reviewed by Schwarz and Datema, 1984; Fuhrmann et al., 1985). In these experiments, different trimming inhibitors were used to investigate the localization of HIV-2 glycoprotein precursors and also to study the role of glycosylation in the processing of the envelope precursor. The inhibitors used were:

castanospermine, a plant alkaloid that inhibits glucosidase I (Saul et al., 1983);

deoxynojirimycin (dNM), a glucose analogue that inhibits trimming glucosidase I and II (Lemansky et al., 1984);

1-deoxymannojirimycin (dMM), a mannose analogue that inhibits mannosidase catalyzed reactions (Fuhrmann et al., 1984);

bromoconduritol (6-bromo-3,4,5-trihydroxycyclohex-1-ene) that inhibits glucosidase II (Datema et al., 1982); and swainsonine, an indolizidine alkaloid that inhibits Golgi mannosidase II (Tulsiani et al., 1982).

Specifically, HIV-2 infected CEM cells were labeled (16 hours, 37° C.) with $^{35}$S-methionine (200 μCi/ml; 4×10⁶ cells/ml) in the absence (lanes T, FIG. 7) or presence of the oligosaccharide trimming inhibitor 1 mM bromoconduritol (lanes Bro, FIG. 7);

1 mM castanospermine (lanes Cast, FIG. 7);

10 μg/ml swainsonine (lanes Sw, FIG. 7);

3 mM deoxynojirimycin (lanes dNM, FIG. 7); and 1 mM deoxymannojirimycin (lanes dMM, FIG. 7).

Extracts from infected cells (panel CELL) and from culture medium containing virus particles (panel SN) were purified on HIV-2 serum-Sepharose to identify viral glycoproteins gp125, gp140, and gp300 in infected cells and gp125 in culture medium. All samples were analyzed by polyacrylamide (7.5%) gel electrophoresis.

In order to show that inhibition of gp125 production by cells treated with different inhibitors is specific to the viral glycoprotein, culture media were assayed for viral core protein p26 by an immunoprecipitation assay using an HIV-2-seropositive serum (Clavel et al., 1986a, 1987). The p26 was analyzed by polyacrylamide (12.5%) gel electrophoresis. FIG. 7 represents a fluorograph showing only one part of each gel.

As expected, control infected cells contained gp300, gp140, and gp125 whereas only gp125 was observed in the extracellular medium (FIG. 7, sections cell and SN, lanes T). In cells treated with castanospermine or dNM, there was a normal level of gp300, no gp125 and a small amount of a 150 Kd protein that probably corresponds to the glucosylated form of gp140. In such cells, therefore, the processing of the envelope glycoprotein was blocked since no gp125 was detectable in the extracellular medium in spite of the production of p26, the core protein of HIV-2 (FIG. 7, lanes Cast and dNM). These results indicate that removal of the terminal glucose residues from the oligosaccharide chains of the envelope glycoprotein precursor is necessary for its processing and cleavage by the cellular protease.

Bromoconduritol, which acts on glucosidase II, also inhibited by 70-90% the normal production of gp125, but the levels of gp140 and gp300 remained normal (FIG. 7, lanes Bro). In contrast to castanospermine and dNM (which inhibit removal of terminal glucose residue), bromoconduritol treatment (which inhibits removal of two inner glucose residues) did not block completely the processing of HIV-2 envelope glycoprotein. In fact, low amounts of gp125 were detectable intracellularly and extracellularly. This latter result suggests that a low level of mannose trimming can occur without removal of the two inner glucose residues. Such a phenomenon has been observed previously for the processing of other viral glycoproteins during bromoconduritol treatment (Datema et al., 1982).

Mannosidase inhibitors, swainsonine and dMM, did not cause an apparent modification in the level of intracellular gp300, gp140, and gp125, but the level of extracellular gp125 was 50% less than that from the corresponding control cells (FIG. 7, lanes Sw and dMM). Thus, although the oligosaccharide chain was only deglucosylated, the glycoprotein precursor was proteolytically cleaved to yield a protein similar to gp125 but with a higher content of mannose, which probably affected the cellular transport of gp125. The molecular weight of the extracellular glycoprotein produced in the presence of dMM was slightly higher than that produced in the absence of the inhibitor. This is probably due to the higher content of mannose residues in the extracellular protein synthesized by dMM-treated cells (FIG. 7, section SN).

It should be emphasized that the effects of trimming enzyme inhibitors on the processing of HIV-2 envelope glycoprotein were specific since the synthesis (data not shown) and the production of HIV-2 p26 was not affected at all (FIG. 7, section SN).

Figure 8A:
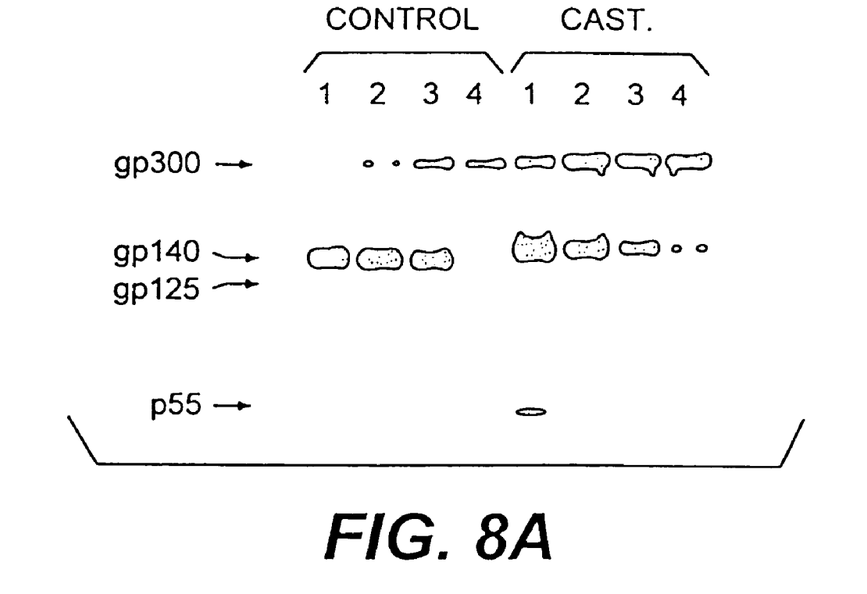
FIGS. 8A and 8B depict the results of electrophoresis of HIV-2 glycoproteins obtained during pulse-chase experiments in HIV-2 infected CEM cells in the absence (control) or presence of castanospermine (FIG. 8A) or monensin (FIG. 8B)

H. Effect of Castanospermine and Monensin on the Processing of HIV-2 Glycoproteins (FIG. 8)

To study the intracellular processing of HIV-2 glycoproteins, pulse-chase experiments were performed. The results are shown in FIG. 8. More particularly, the experiments were carried out as follows:

(a) Pulse-chase experiments were performed in HIV-2 infected CEM cells in the absence (Control) or presence of 1 mM castanospermine (Cast.). Control: infected cells were incubated-1 hour at 37° C. in methionine-free medium before 15 minutes pulse labeling with $^{35}$S-methionine (200 µCi/ml; 4×10$^5$ cells/ml; lane 1, FIG. 8a). The radioactive label was then chased in culture medium containing 5 mM cold methionine for 0.5, 1.5, and 3 hours (in lanes 2, 3, and 4, respectively, FIG. 8a). Cast.: HIV-2 infected CEM cells were incubated (1 hour, 37° C.) in methionine-free medium containing castanospermine before 30 minutes pulse labeling with $^{35}$S-methionine (lane 1, FIG. 8a). These cells were then chased as above, but in the presence of castanospermine for 0.5, 1.5, and 3 hours (lanes 2, 3, and 4, respectively, FIG. 8a).

The gp140 was the first protein detectable 15 minutes after pulse labeling. During the chase, gp300 became detectable at 0.5 hours, whereas gp125 became detectable at 1.5-3 hours. The fact that gp300 was observed after synthesis of gp140 and the fact that gp125 was detectable only after formation of gp300 (FIG. 8A, lanes 1-4), suggest that dimerization is an intermediate step necessary for the oligosaccharide processing towards the mature glycoprotein, gp125. This suggestion was confirmed by the use of castanospermine, which inhibits the trimming of the external glucose residue of polysaccharide chains.

After 30 minutes of pulse labeling in the presence of castanospermine, a 150 Kd protein was detectable along with gp300 (FIG. 8, Cast., lane 1). The 150 Kd protein should correspond to gp140; the slight increase in the molecular weight of the first precursor is ascribed to the presence of glucose residues in its oligosaccharide chains. Thus, gp140 synthesized in HIV-2 infected cells represents the precursor glycoprotein without its glucose residues. Accordingly, the 150 Kd protein (gp150) represents the first immature glycoprotein of HIV-2 envelope. The removal of glucose residues in control cells has been reported to be a rapid process occurring during or briefly after cotranslational translocation of precursor glycoproteins into endoplasmic reticulum (Lemansly et al., 1984). After 30 minutes of pulse and 3 hours of chase in the presence of castanospermine, the level of gp150 was gradually reduced while gp300 accumulated (FIG. 8, Cast, lanes 1-4). Under these conditions, the precursor was not cleaved to yield gp125.

Figure 8B:
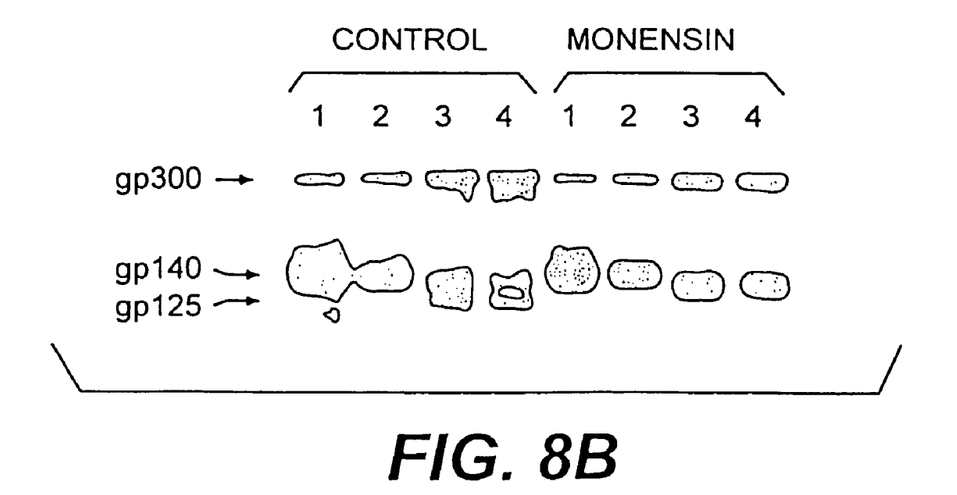

Further characterization of HIV-2 envelope glycoprotein was studied in pulse-chase experiments using monensin, a cationic ionophore that inhibits the transport of proteins from Golgi to the plasma membrane or in some cases it might even block the transport of proteins at the level of the medial Golgi cisternae (Tartakoff and Vassali, 1977; Johnson and Schlesinger, 1980; Strous and Lodish, 1980; Griffiths et al., 1983). HIV-2 infected cells in the absence or presence of monensin were pulsed labeled as follows:

(b) Pulse chase experiments in HIV-2 infected cells were carried out in the absence (Control) or presence of 1 µM monensin. Infected cells with or without monensin were incubated (1 hour, 37° C.) in methionine-free medium before 30 minutes pulse labeling with $^{35}$S-methionine (lanes 1, FIG. 8b). Labeled cells were then chased in culture medium containing 5 mM cold methionine for 0.5, 1.5, and 3 hours (lanes 2, 3, and 4, respectively, FIG. 8b). Extracts were purified on HIV-2 serum-Sepharose, and labeled proteins were analyzed by polyacrylamide (7.5%) gel electrophoresis. Fluorographs are shown in FIG. 8b. (The p55 shows the gag precursor in section A, lanes 1.)

In the presence of monensin, HIV-2 infected cells synthesized normal levels of gp140 and its dimeric form. However, no gp125 was detectable in monensin treated cells. After 1.5-3 hours of chase, monensin treated cells accumulated a 135 Kd protein (gp135) that is probably the dissociated product of the dimer precursor. The slightly smaller molecular weight of gp135 might be accounted for by the removal of some mannose residues by the action of RER and Golgi mannosidases. In view of these results, it is tempting to speculate that after deglucosylation, gp300 becomes trimmed by mannosidases of RER and Golgi before its dissociation into the mature precursor gp135 of HIV-2 envelope. This gp135 could then be transported to plasma membrane and also be cleaved by cellular protease. Inhibition of protein-transport by monensin blocks the mature glycoprotein gp135 in trans Golgi. No mature envelope glycoproteins are detectable in monensin treated cells, intracellularly or extracellularly, although p26 is synthesized and excreted (data not shown).

I. Dimerization of the Glycoprotein Precursor Occurs also in SIVmac Infected Cells (FIG. 9)

The nucleotide sequence of HIV-2 envelope shows a considerable homology (75% amino acid identity) to that of SIV (Guyader et al., 1987; Chakrabarti et al., 1987; Franchini et al., 1987). For this reason, it was important to investigate whether dimerization of envelope glycoproteins is detectable in SIV infected cells. SIV proteins were purified by the immunoaffinity column containing antibodies specific for HIV-2 proteins, since the gag, pol, and env proteins of HIV-2 and SIV are antigenically cross-reactive.

More particularly, SIV-infected HUT-78 cells were labeled (16 hours, 37° C.) with $^{35}$S-methionine (200 µCi/µl; 4×10$^6$ cells/ml), $^3$H-fucose (200 µCi/µl; 4×10$^6$ cells/ml) and $^{14}$C-mannose (25µCi/µl; 4×10$^6$ cells/ml). Extracts from infected cells (lanes C, FIG. 9) and from the culture medium containing SIV (lanes V, FIG. 9) were purified on HIV-2 serum-Sepharose. Because of cross-reactivity between HIV-2 and SIV proteins, the HIV-2 positive serum could be used to immunoprecipitate SIV proteins. All samples were analyzed by polyacrylamide (7.5%) gel electrophoresis. (See "Experimental Procedures".) A fluorograph of the different gels is shown in FIG. 9.

Figure 9:
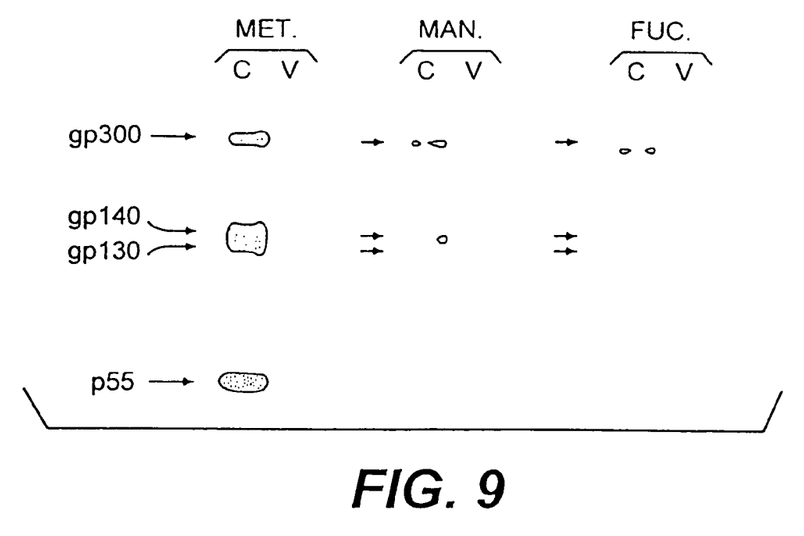
FIG. 9 is a fluorograph of polyacrylamide gels after electrophoresis of SIV envelope glycoproteins labeled with $^{35}$S-methionine, $^{3}$H-fucose, or $^{14}$C-mannose.

FIG. 9 shows that SIV infected cells synthesize three high molecular weight proteins analogous to those synthesized in HIV-2 infected cells: gp300, gp140, and gp130. The electrophoretic mobility of gp300$_{SIV}$ and gp140$_{SIV}$ correspond to that of HIV-2 glycoproteins gp300 and gp140 (data not shown). The gp130$_{SIV}$ has a slightly higher mobility than gp125 of HIV-2. The p55 labeled with $^{35}$S-methionine is probably the gag precursor of SIV.

Evidence that these proteins present in SIV infected cells are glycoproteins was provided by the isotopic labeling with $^{14}$C-mannose and $^3$H-fucose. All the three proteins incorporated mannose, but only gp300$_{SIV}$ and gp130$_{SIV}$ incorporated fucose (FIG. 9). The gp300$_{SIV}$ and gp140$_{SIV}$ are intracellular proteins, whereas gp130$_{SIV}$ is the extracellular glycoprotein.

The fact that gp300$_{SIV}$ and gp130$_{SIV}$ can incorporate fucose suggests that they are processed products of gp140$_{SIV}$.

These results indicate that doublet formation of the envelope glycoprotein precursor is a specific property of HIV-2 and SIV envelope gene expression. It should be emphasized that HIV-1 envelope glycoprotein does not undergo dimerization during its processing. HIV-1 infected cells in the presence of castanospermine or dNM do not accumulate envelope dimers (data not shown) as it is the case for HIV-2 or SIV.

This invention thus describes for the first time the processing of HIV-2 envelope glycoproteins and details a novel mechanism of glycoprotein processing with N-linked oligosaccharide chains. The envelope glycoproteins of HIV-2, i.e. the extracellular gp125 and transmembrane gp36, arise from a common precursor glycoprotein (Guyader et al., 1987). The unusual feature of this glycoprotein precursor is that it requires the formation of a homologous dimer in order to become transported and processed through the Golgi apparatus. The mechanism of dimerization of envelope glycoprotein is not entirely clear. The fact that the purified dimer can be dissociated at an acidic pH (pH 6.0) suggests that dimerization might be pH dependent. Oligosaccharide chains on the precursor glycoprotein are not essential for dimer formation. Evidence for this has been obtained by two different experiments: (1) Digestion with endo H results in a shift in the electrophoretic mobility of the dimer without dissociating it; and (2) In the presence of tunicamycin, HIV-2 infected cells synthesize an unglycosylated envelope precursor (80-90 Kd) that can form a dimer (200 Kd). These results emphasize that the dimer formation is an intrinsic property of the polypeptide moiety of the envelope precursor.

Pulse-chase experiments in the absence or presence of castanospermine (FIG. 8) suggest that dimerization of the glycoprotein precursor normally occurs immediately after removal of glucose residues. Since glucosidases are associated with membranes of endoplasmic reticulum, then it is most likely that dimerization occurs in the RER. In the presence of castanospermine, the dimer becomes accumulated in RER and it is not processed. However, once the glucose residues are removed, then inhibition of the RER mannosidase does not prevent the processing of the glycoprotein-dimer through the Golgi apparatus (FIG. 7). Accordingly, the glucose residues in the oligosaccharide chains of the dimer precursor prevent its exit from the RER. In accord with this, it has been postulated that glucose trimming is necessary for efficient transport from the RER to the Golgi, possibly because the deglucosylated oligosaccharide forms part of a recognition site for a transport receptor (Lodish and Kong, 1984; Lemansky et al., 1984). It might also be possible that glucose removal is crucial for the precursor dimer to achieve a correct functional configuration (Schlesinger et al., 1984) that favors the action of trimming mannosidases.

Figure 10:
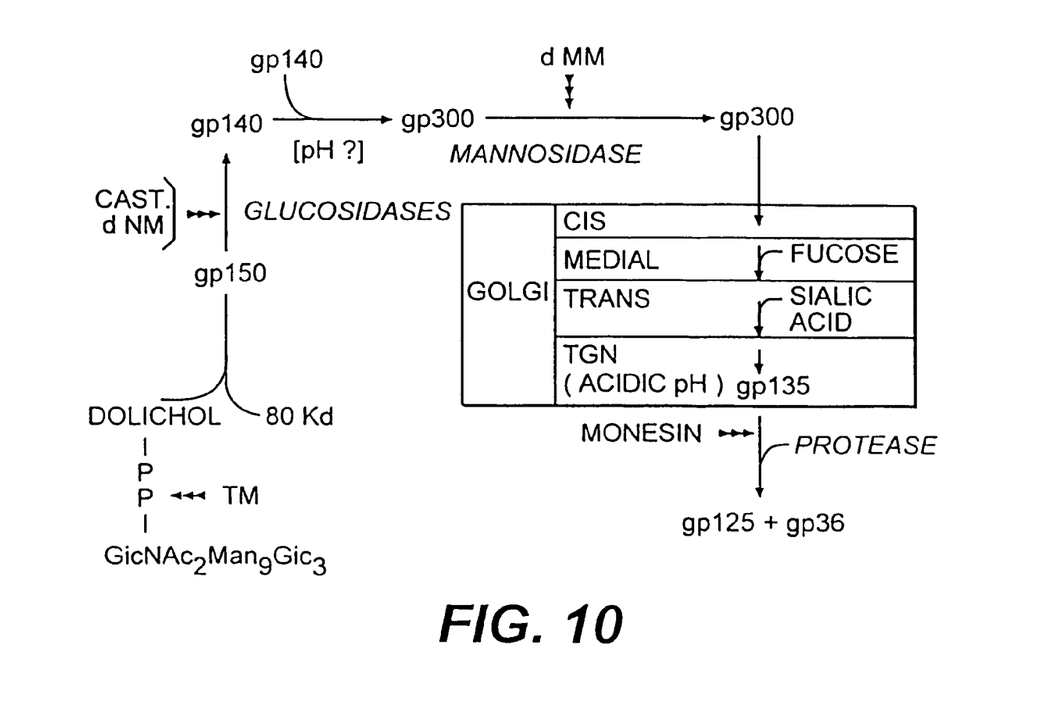
FIG. 10 is a schematic pathway postulated for in vivo processing of HIV-2 envelope glycoprotein.

In view of these results, a schematic pathway for the processing of HIV-2 envelope glycoproteins is proposed in FIG. 10. With reference to FIG. 10, the expected size of the polypeptide moiety of the precursor envelope glycoprotein is about 80 Kd (FIGS. 4 and 6). The oligosaccharide chain is transferred from dolichol-P-P to the newly synthesized envelope precursor (80 Kd) probably at acceptor amino-acid asparagine residues (Kornfeld and Kornfeld, 1985). As depicted in FIG. 10, tunicamycin inhibits assembly of dolichol-P-P glycan, and for this reason the 80 Kd protein does not become glycosylated.

Addition of oligosaccharide chains to the 80 Kd protein yields the first envelope glycoprotein precursor, gp150. This precursor might or might not exist as such in infected cells, since addition of polysaccharide chains and glucose trimming probably occurs during translation of the precursor. Whatever is the case, gp150 becomes rapidly deglucosylated to give gp140. At this stage, a difference in environment, perhaps of pH, would trigger dimer formation by the fusion of two gp140 molecules. The resulting gp300 can then be trimmed by the RER mannosidase and transported to the Golgi apparatus.

In the presence of castanospermine or dNM, gp150 becomes dimerized and is accumulated in the RER. This dimer is not processed because it is glucosylated. However, as long as the dimer is found in the deglucosylated form, it can be transported to the Golgi; inhibition of RER mannosidase by dMM does not block processing of the dimer precursor.

In the Golgi, gp300 traverses the different compartments probably by vesicular transport (Griffiths and Simons, 1986) during which the oligosaccharide chain is further trimmed by Golgi mannosidases before addition of other sugars such as fucose and sialic acid. Evidence for fucose incorporation has been obtained by isotopic labeling of gp300 with $^3$H-fucose. Evidence for sialic acid incorporation was obtained indirectly by digesting gp300 with neuraminidase, an enzyme that hydrolyzes terminal N-acetylneuraminic acid in various glycoproteins (Peyrieras et al., 1983). The gp300 of HIV-2 is susceptible to digestion with neuraminidase as evidenced by a significant decrease in the electrophoretic mobility of the dimer (data not shown). The results are consistent with the precursor keeping its dimeric form all through its processing in the Golgi cis, medial, and trans cisternae before its transport to the trans-Golgi network (TGN; Griffiths and Simons, 1986) where it dissociates due to a drop in the pH of this compartment.

The dissociated dimer yields glycoproteins (gp135) of slightly smaller molecular weight than the first detectable glycoprotein precursor (gp150-140). The gp135 could then be transported to plasma membrane and also be cleaved by the cellular protease to yield the mature glycoproteins of HIV-2 envelope, gp125, and gp36. Monensin most probably inhibits transport from the Golgi to the plasma membrane; for this reason gp135 accumulates in the Golgi.

It is well accepted that the Golgi apparatus is implicated in the mechanism of sorting secretory and plasma membrane proteins, which seems to take place in the last Golgi compartment referred to as TGN (Griffiths and Simons, 1986). This compartment on the trans side of the Golgi stack, previously has been referred to as Golgi endoplasmic reticulum lysosomes (GERL) and recently as post-Golgi vacuoles or the trans-most cisternae of the Golgi stack (Novikoff, 1976; Saraste and Kuismanen, 1984; Orci et al., 1987). Interestingly, the pH of the TGN has been considered to be mildly acidic, i.e., about pH 6 (Anderson and Pathak, 1985; Griffiths and Simons, 1986). The acidic pH in the TGN could then account for the dissociation of the processed dimer.

The results discussed here illustrate that the processing of the envelope glycoproteins of HIV-2 is a multistep process involving the synthesis of an immature precursor gp150-140, the intermediary dimer precursor gp300 and finally the mature precursor gp135. Despite their evolutionary relationship, HIV-1 and HIV-2 have found different mechanisms for the processing of their envelope glycoproteins. Whether or not these differences are involved in their pathogenesis is under investigation.

Following is a more detailed description of the experimental procedures used in this invention.

II. Experimental Procedures

A. Materials

L-($^{35}$S)Methionine (specific activity 1000 Ci/mmol, L-(6-$^3$H) Fucose (specific activity: 45-70 Ci/mmol), D-(6-$^3$H)Glucosamine (specific activity: 20-40 Ci/mmol and D-(U-$^{14}$C) Mannose (specific activity: 200-300 mCi/mmol) were purchased from Amersham (Amersham, UK). Bromoconduritol, castanospermine, 1-deoxymannojirimycin (dMM), 1-deoxynojirimycin (dNM), swainsonine and tunicamycin were obtained from Boehringer-Mannheim (Mannheim, West Germany). Endo B-N-acetylglucosaminidase H was from Calbiochem (San Diego, USA). Ampholines were purchased from Pharmacia (Uppsala, Sweden).

B. Virus and Cells

HIV-1$_{BRU}$ isolate of the human immunodeficiency virus type 1 (Montagnier et al., 1984), HIV-2$_{ROD}$ isolate of the human immunodeficiency virus type 2 (Clavel et al., 1986a), and Simian immunodeficiency virus, SIVmac$_{142}$ (Daniel et al., 1985), were used in this study.

The different cell lines and human lymphocytes were cultured in suspension medium RPMI-1640 (GIBCO-BRL, Cergy-Pontoise, France) containing 10% (v/v) fetal calf serum; 2 µg/ml polybrene (Sigma) was added for HIV infected cell cultures. CEM clone 13 cells are derived from the human lymphoid cell line CEM (ATCC-CCL119) and express the T4 antigen to a high level. Five days after infection with HIV-1$_{BRU}$ or HIV-2$_{ROD}$ isolates, about 80-90% of the cells produce viral particles and can be identified by a cytopathic effect corresponding to vacuolization of cells and appearance of small syncytia.

The HUT-78 cell line is another human T4 positive lymphoid cell line (Gadzudar et al., 1980) that is highly permissive for the replication of SIVmac$_{142}$ (Daniel et al., 1985). Peripheral blood lymphocytes from healthy blood donors were stimulated for three days with 0.2% (w/v) phytohemagglutinin fraction P (Difco, Detroit, USA) in RPMI-1640 medium supplemented with 10% fetal calf serum. Cells were then cultured in RPMI-1640 medium containing 10% (v/v) T cell growth factor (TCGF, Biotest). After infection with HIV-2, lymphocytes were cultured in presence of 10% (v/v) TCGF and 2 µg/ml Polybrene.

C. Metabolic Labeling of Cells

For metabolic labeling of proteins, infected cells were incubated for 16 hours at 37° C. in MEM culture medium without L-methionine and serum but supplemented with 200 µCi/ml $^{35}$S-methionine. For metabolic labeling of glycoproteins, infected cells were incubated for 16 hours at 37° C., in MEM culture medium lacking serum and glucose but supplemented with 200 µCi/ml $^3$H-fucose or 200 µCi/ml $^3$H-glucosamine or 25 µCi/ml $^{14}$C-mannose.

D. Cell and Viral Extracts

Cell pellets corresponding to 10$^7$ cells were resuspended in 100 µl of buffer: 10 mM Tris-HCl pH 7.6, 150mM NaCl, 1 mM EDTA, 0.2 mM PMSF, 100 units/ml aprotinin (Iniprol, Choay) before addition of 100 µl of the same buffer containing 2% (v/v) Triton X-100. Cell extracts were centrifuged at 12,000 g for 10 minutes, and the supernatant was stored at −80° C. until used. For viral extract preparations, 100 µl of 10X lysis buffer (100 mM Tris-HCl pH 7.6, 1.5M NaCl, 10 mM EDTA, 10% (v/v) Triton X-100, 100 units/ml aprotinin) was added per ml of clarified supernatant from infected CEM cells and processed as above.

E. Preparation of an Inmnunoadsorbant with Antibodies from an HIV-2 Seropositive Patient Sera Immunoglobulins from the serum of an HIV-2 seropositive patient were precipitated with 50% (NH$_4$)$_2$S0$_4$, dissolved in 20 mM sodium phosphate (pH 8.0) and further purified on a DEAE cellulose column (DE 52, Whatman) by elution with 20 mM sodium phosphate (pH 8.0). Immunoglobulins purified in this manner were judged to be 90% pure. The antibodies were subsequently coupled to CNBr-activated Sepharose CL 4B according to a technique described by Berg (1977). Two milligrams of IgG were coupled per ml of Sepharose CL 4B. This immunoadsorbant is referred to as HIV-2 serum-Sepharose.

F. Binding of the HIV-2 Proteins on the Immunoaffinity Column

Cell extracts from HIV-2 producing CEM cells were first diluted in two volumes of binding buffer (20 mM Tris-HCl pH 7.6, 50 mM KCl, 150 mM NaCl, 1 mM EDTA, 1% (v/v) Triton X-100, 20% (v/v) glycerol, 7 mM mercaptoethanol, 0.2 mM PMSF, 100 units/ml aprotinin) before incubation with one volume of HIV-2 serum-Sepharose. Supernatants from HIV-2 producing cells were processed as cell extracts except that only one tenth of binding buffer concentrate 10X was added per volume of supernatant. The binding was carried out overnight, then the column was washed batchwise in binding buffer. Proteins bound to the column were eluted by boiling in electrophoresis sample buffer (125 mM Tris-HCl pH 6.8, 1% (w/v) SDS, 2M urea, 20% glycerol, 1% β-mercaptoethanol). Eluted proteins were resolved by electrophoresis on 7.5% polyacrylamide-SDS gels containing 6M urea and 0.1% bisacrylamide instead of 0.2% (w/v).

G. Preparative Electrophoresis

HIV-2 glycoproteins eluted from the affinity column were resolved by polyacrylamide gel electrophoresis as previously described, and the regions of the gel containing the viral glycoproteins were cut out by reference to the position of prestained molecular weight protein markers (BRL).

Glycoproteins were eluted by incubation for 16 hours at 4° C. in elution buffer (0.1M NaHCO$_3$, 0.5 mM EDTA, 0.05% (w/v) SDS, 0.2 mM PMSF). The glycoprotein fractions thus obtained were lyophilized and kept refrigerated until used.

H. Two Dimensional Electrophoresis

Two dimensional gel electrophoresis was performed as described by O'Farrel (1975) with the following modification: L-($^{35}$S)-methionine labeled proteins bound on the HIV-2 serum-Sepharose column were eluted by boiling in electrophoresis sample buffer as previously described before dilution in a volume of buffer containing 9.5M urea, 8% (v/v) mercaptoethanol, 1.6% (w/v) ampholines pH ranges 6.5-9, 0.4% (w/v) ampholines pH ranges 3-10, and 100 units/ml aprotinin.

It will be understood that the present invention is intended to encompass the previously described proteins and glycoproteins in purified form, whether or not fully glycosylated, and whether obtained using the techniques described herein or other methods. In a preferred embodiment of this invention, the polypeptides are substantially free of human tissue and human tissue components, nucleic acids, extraneous proteins and lipids, and adventitious microorganisms, such as bacteria and viruses. It will also be understood that the invention encompasses equivalent proteins and glycoproteins having substantially the same biological and immunogenic properties. Thus, this invention is intended to cover serotypic variants of the proteins and glycoproteins of the invention.

The proteins and glycoproteins of this invention can be obtained by culturing HIV-2 in susceptible mammalian cells of lymphocytic lineage, such as T-lymphocytes or pre-T-lymphocytes of human origin or non-human primate origin (e.g. chimpanzee, African green monkey, or macaques.) A number of different lymphocytes expressing the CD4 phenotypic marker can be employed. Examples of suitable target cells for HIV-2 infection are mononuclear cells prepared from peripheral blood, bone marrow, and other tissues from patients and donors. Alternatively, established cell lines can be employed. For example, HIV-2 can be propagated on blood-donor lymphocyte cultures, followed by propagation on continuous cell strains of leukemic origin, such as HUT 78. HUT 78 is a well characterized mature human T cell line, which has been deposited at Collection Nationale Des Cultures De Microorganismes (C.N.C.M.) at the Institut Pasteur in Paris, France on Feb. 6, 1986, under culture collection deposit accession number C.N.C.M. 1-519. Another suitable target for HIV-2 infection and production of the proteins and glycoproteins of the invention is the T-cell line derived from an adult with lymphoid leukemia and termed HT. HT cells continuously produce virus after parental cells are repeatedly exposed to concentrated cell culture fluids harvested from short-term culture T-cells grown in TCGF that originated from patients with LAS or AIDS. In addition, there are several other T or pre-T human cell lines, such as CEM and MOLT 3, that can be infected and continue to produce HIV-2. Furthermore, B-lymphoblastic cell lines can also be productively infected by HIV. Montagnier et al., *Science,* 225: 63-66 (1984).

The proteins and glycoproteins of the invention can be produced in the target cells using the culture conditions previously described, as well as other standard techniques. For instance, infected human lymphocytes can be stimulated for three days by phytohemaglutinin (PHA). The lymphocytes can be cultured in RPMI-1640 medium to which has been added 10% fetal calf serum, $10^{-5}$M beta-mercaptoethanol, interleukin-2, and human alpha anti-interferon serum. Barre-Sinoussi et al., *Science,* 220: 868-871 (1983). In addition, techniques for the propagation of HIV-2 in HUT 78 and CEM cell lines are described in U.S. application Ser. No. 835,228, filed Mar. 3, 1986, now U.S. Pat. No. 4,839,288, the entire disclosure of which is relied upon and specifically incorporated by reference.

The production of virus in the cell cultures can be monitored using several different techniques. Supernatant fluids in the cell cultures can be monitored for viral reverse transcriptase activity. Electron microscopic observation of fixed and sectioned cells can also be used to detect virus. In addition, virus can be detected by transmitting the virus to fresh normal human T-lymphocytes (e.g., umbilical cord blood, adult peripheral blood, or bone marrow leukocytes) or to established T-cell lines. Testing for antigen expression by indirect immunofluorescence or Western Blot procedures using serum from seropositive donors can also be employed. In addition, nucleic acid probes can be utilized to detect viral production.

After a sufficient period of time for viral multiplication to take place, infected cells can be separated from the culture medium and disrupted to expose intracellular proteins using conventional techniques. For example, physical shearing, homogenization, sonication, detergent solubilization, or freeze-thawing can be employed. The viral proteins released by these cells can be separated from the other cellular components and purified using standard biochemical procedures. For example, proteins can be separated from the live virus by centrifugation, and the proteins can then be purified by ultracentrifugation, gel filtration, ion-exchange chromatography, affinity chromatography, dialysis, or by the use of monoclonal antibodies or by combinations of these procedures. A thorough purification of the antigens of the invention can be performed by immunoreaction with the sera of patients known to possess antibodies effective against the antigens, with concentrated antibody preparations such as polyclonal antibodies, or with monoclonal antibodies directed against the antigens of the invention.

The proteins and the glycoproteins of the present invention can be used as antigens to identify antibodies to HIV-2 and SIV in materials and to determine the concentration of the antibodies in those materials. Thus, the antigens can be used for qualitative or quantitative determination of the retrovirus in a material. Such materials of course include human tissue and human cells, as well as biological fluids, such as human body fluids, including human sera. When used as a reagent in an immunoassay for determining the presence or concentration of the antibodies to HIV-2, the antigens of the present invention provide an assay that is convenient, rapid, sensitive, and specific.

More particularly, the antigens of the invention can be employed for the detection of HIV-2 by means of immunoassays that are well known for use in detecting or quantifying humoral components in fluids. Thus, antigen-antibody interactions can be directly observed or determined by secondary reactions, such as precipitation or agglutination. In addition, immunoelectrophoresis techniques can also be employed. For example, the classic combination of electrophoresis in agar followed by reaction with antiserum can be utilized, as well as two-dimensional electrophoresis, rocket electrophoresis, and immunolabeling of polyacrylamide gel patterns (Western Blot or immunoblot.) Other immunoassays in which the antigens of the present invention can be employed include, but are not limited to, radioimmunoassay, competitive immunoprecipitation assay, enzyme immunoassay, and immunofluorescence assay. It will be understood that tubidimetric, calorimetric, and nephelometric techniques can be employed. An immunoassay based on Western Blot technique is preferred.

Immunoassays can be carried out by immobilizing one of the immunoreagents, either an antigen of the invention or the antibodies to the antigen, on a carrier surface while retaining immunoreactivity of the reagent. The reciprocal immunoreagent can be unlabeled or labeled in such a manner that immunoreactivity is also retained. These techniques are especially suitable for use in enzyme immunoassays, such as enzyme linked immunosorbent assay (ELISA) and competitive inhibition enzyme immunoassay (CIEIA).

When either the antigen of the invention or antibody to the antigen is attached to a solid support, the support is usually a glass or plastic material. Plastic materials molded in the form of plates, tubes, beads, or disks are preferred. Examples of suitable plastic materials are polystyrene and polyvinyl chloride. If the immunoreagent does not readily bind to the solid support, a carrier material can be interposed between the reagent and the support. Examples of suitable carrier materials are proteins, such as bovine serum albumin, or chemical reagents, such as glutaraldehyde or urea. Coating of the solid phase can be carried out using conventional techniques.

Depending on the use to be made of the proteins and glycoproteins of the invention, it may be desirable to label them. Examples of suitable labels are radioactive labels, enzymatic labels, fluorescent labels, chemiluminescent labels, and chromophores. The methods for labeling proteins and glycoproteins of the invention do not differ in essence from those widely used for labeling immunoglobulin. The need to label may be avoided by using labeled antibody to the antigen of the invention or anti-immunoglobulin to the antibodies to the antigen as an indirect marker.

Once the proteins and glycoproteins of the invention have been obtained, they can be used to produce polyclonal and monoclonal antibodies reactive therewith. Thus, a protein or glycoprotein of the invention can be used to immunize an animal host by techniques known in the art. Such techniques usually involve inoculation, but they may involve other modes of administration. A sufficient amount of the protein or the glycoprotein is administered to create an immunogenic response in the animal host. Any host that produces antibodies to the antigen of the invention can be used. Once the animal has been immunized and sufficient time has passed for it to begin producing antibodies to the antigen, polyclonal antibodies can be recovered. The general method comprises removing blood from the animal and separating the serum from the blood. The serum, which contains antibodies to the antigen, can be used as an antiserum to the antigen. Alternatively, the antibodies can be recovered from the serum. Affinity purification is a preferred technique for recovering purified polyclonal antibodies to the antigen from the serum.

Monoclonal antibodies to the antigens of the invention can also be prepared. One method for producing monoclonal antibodies reactive with the antigens comprises the steps of immunizing a host with the antigen; recovering antibody-producing cells from the spleen of the host; fusing the antibody-producing cells with myeloma cells deficient in the enzyme hypoxanthine-guanine phosphoribosyl transferase to form hybridomas; selecting at least one of the hybridomas by growth in a medium comprising hypoxanthine, aminopterin, and thymidine; identifying at least one of the hybridomas that produces an antibody to the antigen; culturing the identified hybridoma to produce antibody in a recoverable quantity; and recovering the antibodies produced by the cultured hybridoma.

These polyclonal or monoclonal antibodies can be used in a variety of applications. Among these is the neutralization of corresponding proteins. They can also be used to detect viral antigens in biological preparations or in purifying corresponding proteins, glycoproteins, or mixtures thereof, for example when used in affinity chromatographic columns.

The invention provides immunogenic proteins and glycoproteins, and more particularly, protective polypeptides for use in the preparation of vaccine compositions against HIV-2. These polypeptides can thus be employed as viral vaccines by administering the polypeptides to a mammal susceptible to HIV-2 infection. Conventional modes of administration can be employed. For example, administration can be carried out by oral, respiratory, or parenteral routes. Intradermal, subcutaneous, and intramuscular routes of administration are preferred when the vaccine is administered parenterally.

The ability of the proteins, glycoproteins, and vaccines of the invention to induce protective levels of neutralizing antibody in a host can be enhanced by emulsification with an adjuvant, incorporation in a liposome, coupling to a suitable carrier, or by combinations of these techniques. For example, the proteins and glycoproteins of the invention can be administered with a conventional adjuvant, such as aluminum phosphate and aluminum hydroxide gel, in an amount sufficient to potentiate humoral or cell-mediated immune response in the host. Similarly, the polypeptides can be bound to lipid membranes or incorporated in lipid membranes to form liposomes. The use of nonpyrogenic lipids free of nucleic acids and other extraneous matter can be employed for this purpose.

The immunization schedule will depend upon several factors, such as the susceptibility of the host to infection and the age of the host. A single dose of the vaccine of the invention can be administered to the host or a primary course of immunization can be followed in which several doses at intervals of time are administered. Subsequent doses used as boosters can be administered as needed following the primary course.

The proteins and vaccines of the invention can be administered to the host in an amount sufficient to prevent or inhibit HIV-2 infection or replication in vivo. In any event, the amount administered should be at least sufficient to protect the host against substantial immunosuppression, even though HIV infection may not be entirely prevented. An immunogenic response can be obtained by administering the proteins or glycoproteins of the invention to the host in an amount of about 10 to about 500 micrograms antigen per kilogram of body weight, preferably about 50 to about 100 micrograms antigen per kilogram of body weight. The proteins and vaccines of the invention can be administered together with a physiologically acceptable carrier. For example, a diluent, such as water or a saline solution, can be employed.

In summary, proteins and glycoproteins, which are precursors of HIV-2 and SIV envelope protein, have now been identified. In addition to providing useful tools for detection of antibodies to the retrovirus in humans and for raising neutralizing antibodies to HIV-2 in vitro and in vivo, this invention adds to the base of knowledge relating to immunodeficiency active proteins and glycoproteins of the AIDS viruses. The reference molecular weight was in the form of the following dye markers marketed by BRL Co.:

myosine 200 Kd
phosphorylase B 92.7 Kd
BSA 68 Kd
ovalbumin 43 Kd
alpha chymotrypsin 25.7 Kd
beta lactoglobulin 18.4 Kd
lysozyme 14.3 Kd.

Molecular weights were estimated within an accuracy of about ±10%.

REFERENCES

Anderson, R. G. W. and Pathat, R. K., "Vesicles and Cisternae in the Trans Golgi Apparatus of Human Fibroblasts are Acidic Compartments," *Cell,* 40, 635-643 (1985).

Barré-Sinoussi, F. Chermann, J. C., Rey, F., Nugeyre, M. T., Chamaret, S., Gruest, J., Dauguet, C., Axler-Blin, C., Vézinet-Brun, F., Rouzioux, C., Rozembaum, W., and Montagnier, L., "Isolation of a T-lymphotropic Retrovirus From a Patient at Risk for Acquired Immune Deficiency Syndrome (AIDS)," *Science,* 220, 868-871 (1983).

Berg, K., "Sequential Antibody Affinity Chromatography of Human Leucocyte Interferon," *Scand. J. Immnunol.,* 6, 77-86 (1977).

Brun-Vézinet, F., Rey, M. A., Katlama, C., Girard, P. H., Roulot, D., Yeni, P., Lenoble, L., Clavel, F., Alizon, M., Gadelle, S., Madjar, J. J., and Harzic, M., "Lymphadenopathy-associatied virus type 2 in AIDS and AIDS-related Complex," *Lancet, i,* 128-132 (1987).

Chakrabarti, L., Guyader, M., Alizon, M., Daniel, M. D., Desrosiers, R. C., Thiollais, P., and Sonigo, P., "Sequence of Simian Immunodeficiency Virus from Macaque and its Relationship to Other Human and Simian Retroviruses," *Nature,* 328, 543-547 (1987).

Clavel, F., Guétard, D., Brun-Vézinet, F., Chamaret, S., Rey, M. A., Santos-Ferreira, M. O., Laurent, A. G., Dauguet, C., Katlama, C., Rouzioux, C., Klatzmann, D., Champalimaud, J. L., and Montagnier, L., "Isolation of a New Retrovirus from West African Patients with AIDS," *Science,* 233, 343-346 (1986a).

Clavel, F., Guyader, M., Guétard, D., Sallé, M., Montagnier, L., and Alizon, M., "Molecular Cloning and Polymorphism of the Immune Deficiency Virus Type 2," *Nature,* 324, 691-694 (1986b).

Clavel, F., Mansinho, K., Charet, S., Guétard, D., Favier, V., Nina, J., Santos-Ferreira, M. O., Champalimaud, J. L., and Montagnier, L., "Human Immunodeficiency Virus Type 2

Infection Associated with AIDS in West Africa," *N. Eng. J. Med.*, 316, 1180-1185 (1987).

Dalgleish, A. G., Beverley, P. C., Clapham, P. R., Crawford, D. H., Greaves, M. F., and Weiss, R. A., "The CD4 (T4) Antigen is an Essential Component of the Receptor for the AIDS Retrovirus," *Nature*, 312, 763-767 (1984).

Daniel, M. D., Letvin, N. L., King, N. W., Kannagi, M., Sehgal, P. K. Hunt, R. D., Kanki, P. J., Essex, M., and Desrosiers, R. C., "Isolation of a T-cell Tropic HTLV-III-like Retrovirus from Macaques," *Science*, 228, 1201-1204 (1985).

Datema, R., Romero, P. A., Legler, G., and Schwartz, R. T., "Inhibition of Formation of Complex Oligosaccharides by the Glucosidase Inhibitor Bromoconduritol," *Proc. Natl. Acad. Sci. USA*, 79, 6787-6791 (1982).

Franchini, G., Gurgo, C., Guo, H-G., Gallo, R. C., Collalti, F., Fargnoli, K. A., Hall, L. F., Wong-Staal, F., and Reitz Jr, M. S., "Sequence of Simian Immunodeficiency Virus and its Relationship to the Human Immunodeficiency Viruses," *Nature*, 328, 539-543 (1987).

Fuhrmann, U., Bause, E., Legler, G., and Ploegh, H., "Novel Monnosidase Inhibitor Blocking Conversion of High Mannose to Complex Oligosaccharides," *Nature*, 307, 755-758 (1984).

Fuhrmann, U., Bause, E., and Ploegh, H., "Inhibitors of Oligosaccharide Processing," *Biochimica et Biophysica Acta*, 825, 95-110 (1985).

Fultz, P. N., McClure, H. M., Anderson, D. C., Swenson, R. B., Anand, R., and Srinivasan, A., "Isolation of a T-lymphotropic Retrovirus from Naturally Infected Sooty Mangabey Monkeys (Cercocebusatys)," *Proc. Natl. Acad. Sci. USA*, 83, 5286-5290 (1986).

Gallaher, W. R., "Detection of a Fusion Peptide Sequence in the Transmembrane Protein of Human Immunodeficiency Virus," *Cell*, 50, 327-328 (1986).

Gazdar, A. F., Carney, D. N., Bunn, P. A., Russel, E. K., Jaffe, E. S., Schechter, G. P., and Guccion, J. G., "Mitogen Requirements for the in vitro Production of Cutaneous T-cell Lymphomas," *Blood*, 55, 409-417 (1980).

Griffiths, G., Quinn, P., and Warren G., "Dissection of Golgi Complex: Monensin Inhibits the Transport of Viral Membrane Proteins from Medial to Trans Golgi Cisternae in Baby Hamster Kidney Cells Infected with Semliki Forest virus," *J. Cell. Biol.*, 96, 835-851 (1983).

Griffiths, G. and Simons, R., "The Trans Golgi Network: Sorting at the Exit Site of the Golgi Complex," *Science*, 234, 438-443 (1986).

Guyader, M., Emerman, M., Sonigo, P., Clavel, F., Montagnier, L., and Alizon, M., "Genome Organization and Trans-activation of the Human Immunodeficiency Virus Type 2," *Nature*, 326, 662-669 (1987).

Heifetz, A., Keenan, R. W., and Elhein, A. D., "Mechanism of Action of Tunicamycin on the UDP-GlcNAc: Dolichylphosphate GlcNAc-1-phosphate Transferase," *Biochemistry*, 18, 2186-2192 (1979).

Johnson, D. C. and Schlesinger M. J., "Vesicular Stomatitis Virus and Sindbis Virus Glycoprotein Transport to Cell Surface is Inhibited by Ionophores," *Virology*, 103, 407-424 (1980).

Kannagi, M., Yetz, J. M., and Letvin, N. L., "In vitro Growth Characteristics of Simian T-lymphotropic Virus Type III," *Proc. Natl. Acad. Sci. USA*, 82, 7053-7057 (1985).

Klatzmann, D., Champagne, E., Chamaret, S., Gruest, J. Guétard, D., Hercend, T., Gluckman, J. C., and Montagnier, L., "T. Lymphocyte T4 Molecule Behaves as the Receptor for Human Retrovirus LAV," *Nature*, 312, 767-768 (1984).

Kornfeld, R. and Kornfeld, S., "Assembly of Asparagine-linked Oligosaccharides," *Ann. Rev. Biochem.*, 54, 631-664 (1985).

Kowaslski, M., Potz, J., Basiripour, L., Dorfman, T., Goh, W. C., Terwilliger, E., Dayton, A., Rosen, C., Haseltine, W., and Sodroski, "Functional Regions of the Envelope Glycoprotein of Human Immunodeficiency Virus Type 1," *Science*, 237, 1351-1355 (1987).

Krust, B., Laurent, A. G., Le Guern, A., Jeannequin, O., Montagnier, L., and Hovanessian, A. G., "Characterization of a Monoclonal Antibody Specific for HIV-1 Precursor Glycoprotein," *AIDS*, 2, 17-24 (1988).

Lemansky, P., Gieselmann, V., Hasilik, A., and Von Fugura, K., "Cathespsin D and β-hexosaminidase Synthesized in the Presence of 1-deoxynojirimycin Accumulate in the Endoplasmic Reticulum," *J. Biol. Chem.*, 259, 10129-10135 (1984).

Levy, J. A., Hoffman, A. D., Kramer, S. M., Lanois, J. A., Shimabukuro, J. M., and Oskiro, L. S., "Isolation of Lymphocytopathic Retroviruses from San Francisco Patients with AIDS," *Science*, 225, 840-842 (1984).

Li, E., Tabas, I., and Kornfeld, S., "The Synthesis of Complex-Type Oligosaccharides: Structure of the Lipid-linked Oligosaccharide of the Vesicular Stomatitis Virus G Protein," *J. Biol. Chem.*, 253, 7762-7770 (1978).

Lifson, J. D., Feinberg, M. B., Reyes, G. R., Rabin, L., Banapour B, Chakrabati, S., Moss, B., Wong-Staal, F., Steimer, K. S., and Engleman, E. G., "Induction of CD4-dependent Cell Fusion by the HTLV-III/LAV Envelope Glycoprotein," *Nature*, 323, 725-728 (1986).

Lodish, H. F. and Kong, N., "Glucose Removal from N-linked Oligosaccharides is Required for Efficient Maturation of Certain Secretory Glycoproteins From the Rough Endoplasmic Reticulum to the Golgi Complex," *J. Cell.Biol.*, 98, 1720-1729 (1984).

Marsh, M. and Dalgleish, A., "How do Human Immunodeficiency Viruses Enter Cells?" *Immunology Today*, 8, 369-371 (1988).

McClure, M. O., Marsh, M., and Weiss, R. A., "Human Immunodeficiency Virus Infection of CD4-bearing Cells Occurs by a pH-independent Mechanism," *EMBO J.*, 7, 513-518 (1988).

McDougal, J. S., Mawle, A., Cort, S. P., Nicholson, J. K. A., Cross, G. D., Scheppler-Campbel, J. A., Hicks, D., and Sligh, J., "Cellular Tropism of the Human Retrovirus HTLV-III/LAV: Role of T Cell Activation and Expression of the T4 Antigen," *J. Immunol.*, 135, 3151-3162 (1985).

McDougal, J. S., Kennedy, M. S., Sligh, J. M. Cort, S. P., Mawle, A., and Nicholson, J. K. A., "Binding of HTLV-III/LAV to T4+ Cells by a Complex of the 110 K Viral Protein and the T4 Molecule," *Science*, 231, 382-385 (1986).

Montagnier, L. and Alizon M., "The Human Immune Deficiency Virus (HIV): An Update," *Ann. Inst. Pasteur/Virol.*, 138, 3-11 (1987).

Montagnier, L., Chermann, J. C., Barré-Sinoussi, F., Chamaret, S. Gruest, J., Nugeyre, M. T., Rey, F., Dauguet, C., Axler-Blin, C., Vézinet-Brun, F., Rouzioux, C., Saimot, A. G., Rozembaum, W., Gluckman, J. C., Klatzmann, D., Vilmer, E., Griscelli, C., Gazengel,C., and Brunet, J. B. (1984), "A New Human T-lymphotropic Retrovirus: Characterization and Possible Role in Lymphadenopathy and Acquired Immune Deficiency Syndrome," in *Human T Cell Leukemia/Lymihoma Viruses*, edited by Gallo, R. C., Essex, M. E., and Gross, L., Cold Spring Harbor Laboratory, New York, pp. 363-379 (1984).

Montagnier, L., Clavel, F., Krust, B., Chamaret, S., Rey, F., Barré-Sinoussi, F., and Chermann, J. C., "Identification and Antigenicity of the Major Envelope Glycoprotein of Lymphadenopathy Associated Virus," *Virology,* 144, 283-289 (1985).

Novikoff, A. B., "The Endoplasmic Reticulum: A Cytochemist's View," *Proc. Natl. Acad. Sci. USA,* 73, 2781-2787 (1976).

O'Farrel, P. H., "High Resolution Two-dimensional Electrophoresis of Proteins," *J. Biol. Chem.,* 250, 4007-4021 (1975).

Olden, K., Pratt, R. M., and Yamada, K. M., "Role of Carbohydrates in Protein Secretion and Turnover: Effects of Tunicamycin on the Major Cell Surface Glycoprotein of Chick Embryo Fibroblasts," *Cell,* 13, 461-473 (1978).

Orci, L., Ravazzola, M., Amherdt, A. P., Powel, S. K., Quinn, D. L, and Moore, H-P. H., "The Trans-Most Cisternae of the Golgi Complex: A Compartment for Sorting of Secretory and Plasma Membrane Proteins," *Cell,* 51, 1039-1051 (1987).

Peyrieras, N., Bause, E., Legler, G., Vasilof, R. Claesson, L., Peterson, P., and Ploegh, H., "Effects of Glucosidase Inhibitors Nojirimycin and Deoxynojirimycin on the Biosynthesis of Membrane and Secretory Glycoproteins," *EMBO J.,* 2, 823-832 (1983).

Sonigo, P., Alizon, M., Staskus, K., Klatzmann, D., Cole, S., Danos, O., Retzel, E., Tiollais, P., Haase, A., and Wain-Hobson, S., "Nucleotide Sequence of the Visna Lentivirus: Relationship to the AIDS Virus," *Cell,* 42, 369-382 (1985).

Stein, B. S., Gowda, S. D., Lifson, J. D., Penhallow, R. C., Bensch, K. G., and Engleman, E. G., "pH-independent HIV-entry into CD4-Positive T Cells via Virus Envelope Fusion to Plasma Membrane," *Cell,* 49, 659-668 (1987).

Strous, G. J. A. M. and Lodish, H. F., "Intracellular Transport of Secretory and Membrane Proteins in Hepatoma Cells Infected by Vesicular Stomatitis Virus," *Cell,* 22, 709-717 (1980).

Tarentino, A. L., Plummer, T. H., and Maley, F., "The Release of Intact Oligosaccharides From Specific Glycoproteins By Endo-B-N-Acetyl Glucosaminidase H," *J. Biol. Chem.,* 249, 818-824 (1974).

Tartakoff, A. M. and Vassalli, P., "Plasma Cell Immunoglobulin Secretion: Arrest is Accompanied by Alterations of the Golgi Complex," *J. Exp. Med.,* 146, 1332-1345 (1977).

Wain-Hobson, S., Sonigo, P., Danos, O., Cole, S., and Alizon, M., "Nucleotide Sequence of the AIDS Virus, LAV," *Cell,* 40, 9-17 (1985a).

Wain-Hobson, S., Alizon, M., and Montagnier, L., "Relationship of AIDS to Other Retroviruses," *Nature,* 313, 743 (1985b).

Weiss, R. A., "Receptor Molecule Block HIV," *Nature,* 331, 15 (1988).

What is claimed is:

1. A purified antigenic composition comprising one or more envelope proteins selected from gp300 of HIV-2, p200 of HIV-2, p90/80 of HIV-2, gp300 of SIV, and gp140 of HIV-2.

2. A purified immunogenic composition comprising one or more envelope proteins selected from gp300 of HIV-2, p200 of HIV-2, p90/80 of HIV-2, gp300 of SIV, and gp140 of HIV-2.

3. A method for the preparation of an antigenic glycoprotein gp300 of HIV-2, comprising:

(a) lysing cells infected by a human HIV-2 type retrovirus and separating the supernatant from the cell extract;

(b) incubating the cell extract and/or supernatant on an immunoaffinity column comprising an immuno-absorbent containing purified antibodies obtained from the serum of a patient infected by a human HIV-2 type retrovirus, in the presence of a buffer, to form an antigen-antibody immunological complex;

(c) washing of the column to remove the molecules not retained by the column;

(d) eluting the retained proteins; and (e) recovering the desired antigenic proteins.

* * * * *